United States Patent [19]
Cuppoletti

[11] Patent Number: 6,015,828
[45] Date of Patent: Jan. 18, 2000

[54] CHEMICAL MODIFICATION OF CHLORIDE CHANNELS AS A TREATMENT FOR CYSTIC FIBROSIS AND OTHER DISEASES

[76] Inventor: John Cuppoletti, University of Cincinnati, Intellectual Property Office, 3233 Eden Ave., G-13 Wherry Hall-M.L. 0829, Cincinnati, Ohio 45267-0829

[21] Appl. No.: 08/863,102

[22] Filed: May 23, 1997

Related U.S. Application Data

[60] Provisional application No. 60/018,725, May 31, 1996.

[51] Int. Cl.[7] .......................... A01N 43/50; A01N 33/02; A61K 31/415; A61K 31/13
[52] U.S. Cl. .................................. 514/397; 514/2; 514/8; 514/42; 514/44; 514/62; 514/80; 514/255; 514/383; 514/398; 514/399; 514/400; 514/561; 514/562; 514/563; 514/564; 514/566; 514/638; 514/663; 514/667; 514/673; 514/674; 514/851; 514/311; 514/312; 514/313
[58] Field of Search ..................... 514/397, 398, 514/399, 400, 638, 851, 2, 8, 42, 44, 62, 80, 255, 311, 312, 313, 383, 561, 562, 563, 564, 566, 663, 667, 673, 674

[56] References Cited

U.S. PATENT DOCUMENTS

| | | | |
|---|---|---|---|
| 3,193,523 | 7/1965 | Neumann et al. | 560/2 |
| 3,710,795 | 1/1973 | Higuchi et al. | 424/424 |
| 4,937,270 | 6/1990 | Hamilton et al. | 514/777 |
| 5,240,846 | 8/1993 | Collins et al. | 435/371 |
| 5,242,947 | 9/1993 | Cherksey et al. | 514/626 |
| 5,399,346 | 3/1995 | Anderson et al. | 424/93.21 |
| 5,503,989 | 4/1996 | Bibbs et al. | 435/68.1 |
| 5,504,241 | 4/1996 | Pohl et al. | 560/25 |
| 5,674,898 | 10/1997 | Cheng et al. | 514/557 |
| 5,877,179 | 3/1999 | Pollard et al. | 514/263 |

OTHER PUBLICATIONS

Luis P.Cid, et al., Human Molecular Genetics, 1995, vol. 4, No. 3 pp. 407–413.
Michael J. Welsh, et al, 1992, Neuron, vol. 8, pp. 821–829.
Eduardo F. Tizzano et al., 1992, The Journal of Pediatrics, vol. 120, No. 3, pp. 337–349.
Thomas F. Boat, et al., 'Cystic Fibrosis', The Metabolic Basis of Inherited Disease (1989) Chapter 108, pp. 2649–2680.
Michael R. Knowles, M.D. et al., , Apr., 26, 1990, The New England Journal of Medicine, vol. 322, No. 17, pp. 1189–1194.
Thomas J. Jentsch, 1996, Current Opinion in Neurobiology, pp. 303–310.
Danuta H. Malinowski et al., 1995, the American Physiological Society, 0363–6143/95, pp. C191–C–200.
Thomas J. Jentsch, et al.1995, Journal of Physiology, 482.P, pp. 19S–25S.

*Primary Examiner*—Frederick Krass
*Attorney, Agent, or Firm*—Dinsmore & Shohl LLP

[57] ABSTRACT

This invention relates generally to medical treatment methods. Specifically, the invention relates to methodology for the correction of defective chloride transport by activation of chloride channels of the lung and other epithelia using genetic or chemical modification. These methods relate to the treatment of epithelia with compounds which cause activation of the channel as measured by increased probability (Po) of opening of the channel at physiologically relevant holding potentials. These methods also relate to the treatment of epithelia with gene therapy to introduce chloride channels genes with site mutations which cause activation of the channel as measured by increased probability (Po) of opening of the channel at physiologically relevant holding potentials. These treatments will reduce life-threatening complications frequently found in diseases such as cystic fibrosis. These methods of activation of chloride channels also comprise treatment of chloride channels with amidation reactions.

17 Claims, 6 Drawing Sheets

```
ClC-2G   MAA*PAAAA**VEEGMEPRALQYEQTLMYGRYTQDLGAFAKEEAARIRLGGPEPWRSPPSP       58
ClC-2    ---AT----TVAG--------------------E-------------------KGS--A       61
                                                        D1
ClC-2G   RTPPELLEYGQSRCARCRMCSVRCHKFLVSRVGEDWIFLVLLGLLMALVSWAMDYAIAACL      119
ClC-2    -AT--------------I----------------------------------V--           122
                              D2
ClC-2G   QAQQWMSRGLNTNLLLQYLAWVTYPVVLITFSAGFTQILAPQAVGSGIPEMKTILRGVVLK     180
ClC-2    --------------I---------------------------------------            183
              D3                              D4
ClC-2G   EYLTLKTFVAKVIGLTCALGSGMPLGKEGPFVHIASMCAALLSKFLSLFGGIYENESRNTE     241
ClC-2    ------------------------------------------------------            244
                 D5                                    D6
ClC-2G   MLAAACAVGVGCCFAAPIGGVLFSIEVTSTFFAVRNYWRGFFAATFSAFIFRVLAVWNRDE     302
ClC-2    ------------------------------------------------------            305
                                           D7
ClC-2G   ETITALFKTRFRLDFPFDLQELPAFAVIGIASGFGGALFVYLNRKIVQVMRKQKTINRFLM     363
ClC-2    ------------------------------------------------------            366
              D8
ClC-2G   RKRLLFPALVTLLISTLTFPPGFGQFMAGQLSQKETLVTLFDNRTWVRQGLVEELEPPSTS     424
ClC-2    K----------------------------------------------D-GA----           427
                        D9                      D10
ClC-2G   QAWSPPRANVFLTLVIFILMKFWMSALATTIPVPCGAFMPVFVIGAAFGRLVGESMAAWFP     485
ClC-2    ------------------------------------------------------            488
                                  D11              D12
ClC-2G   DGIHTDSSTYRIVPGGYAVVGAAALAGAVTHTVSTAVIVFELTGQIAHILPVMIAVILANA     546
ClC-2    ------------------------------------------------------            549

ClC-2G   VAQSLQPSLYDSIIRIKKLPYLPELGWGRHQQYRVRVEDIMVRDVPHVALSCTFRDLRLAL     607
ClC-2    ------------------------------------------------------            610
                                                ↓
ClC-2G   HRTKGRTLALVESPESMILLGSIERTQVVALLAAQLSPARRRQSKQKRRVAHTSPPSCQES     668
ClC-2    ------M-----------------S------G----------HM--L-K-QM----D---      671

ClC-2G   PPSPETSVCFQVKAED*****AQGEPHKPLKPALKRGCSNSVNLGESPTGHVESAGIALRS     724
ClC-2    ---S---IR---NT--SGFPG-H-QT----------P--ATS-Q-GT--NM---------      732
                                ↓
ClC-2G   LFCGSPPPE*AASESEKSESSEKRKSKRVRISLASDSDLEGEMSPEEILEWEEQQLDEPVN     784
ClC-2    -------L-STT--L-----CD---L-------------K-----------              793
                                                         D13
ClC-2G   FSDCKIDPAPFQLVERTSLHKTHTIFSLLGVDHAYVTSIGRLIGIVTLKELRKAIEGSVTA     845
ClC-2    ------------------------------------------------------            854

ClC-2G   QGVKVRPPLASFRDSATSSSDTETTEVHALWGPRSRHGLPREGSPSDSDDKCQ              898
ClC-2    -----------------------------T---------                           907
```

FIG. 1

```
-53                                            agtccaggacagagccggaaccgccgagggaggcgagagggcagtgcgcggag 1   ATG GCG GCC GCG GCG GCG GAG GAA GGG ATG GAG CCA CGG GCG CTG CAG CAC GAG
  1    M   A   A   A   A   A   E   E   G   M   E   P   R   A   L   Q   H   E
                              T       A                                   Y 55   CAG ACC CTG ATG TAT GGC CGG TAC ACT CAG GAC CTT GGG GCC TTT GCC AAA GAG
 19    Q   T   L   M   Y   G   R   Y   T   Q   D   L   G   A   F   A   K   E
                                                  E 109   GAA GCT GCT CGG ATT CGC CTG GGA GGG CCT GAA CCC TGG AAA GGT CCC CCT TCC
 37    E   A   A   R   I   R   L   G   G   P   E   P   W   K   G   P   P   S
                                                                      S   #

163   TCT CGG GCT GCC CCA GAG CTC TTG GAA TAT GGA CGG AGC CGT TGC GCC CGA TGC
 55    S   R   A   A   P   E   L   L   E   Y   G   R   S   R   C   A   R   C
                       A           T                       Q

217   CGC GTC TGT TCT GTC CGC TGC CAC AAG TTC CTA GTA TCC AGG GTT GGT GAA GAT
 73    R   V   C   S   V   R   C   H   K   F   L   V   S   R   V   G   E   D
           I       #

271   TGG ATC TTC CTG GTC CTG CTG GGG CTT CTC ATG GCA TTG GTC AGC TGG GTC ATG
 91    W   I   F   L   V   L   L   G   L   L   M   A   L   V   S   W   V   M
      _____D1_____

325   GAC TAT GCC ATT GCT GCC TGT CTG CAA GCC CAG CAG TGG ATG TCC CGG GGC TTG
109    D   Y   A   I   A   A   C   L   Q   A   Q   Q   W   M   S   R   G   L
                              V
      _____

379   AAC ACC AGC ATC TTG CTC CAG TAC CTG GCC TGG GTC ACC TAC CCT GTT GTC CTC
127    N   T   S   I   L   L   Q   Y   L   A   W   V   T   Y   P   V   V   L
       +       N                                         _____D2_____

433   ATC ACT TTC TCA GCC GGA TTC ACA CAG ATC CTG GCC CCT CAG GCT GTC GGC TCT
145    I   T   F   S   A   G   F   T   Q   I   L   A   P   Q   A   V   G   S
      _____

487   GGC ATC CCT GAG ATG AAG ACC ATC TTG CGG GGA GTG GTG CTG AAA GAA TAC CTC
163    G   I   P   E   M   K   T   I   L   R   G   V   V   L   K   E   Y   L

541   ACA CTC AAG ACC TTT ATA GCT AAG GTC ATT GGG CTG ACC TGC GCC CTA GGC AGC
181    T   L   K   T   F   I   A   K   V   I   G   L   T   C   A   L   G   S
       #                   V                       _____D3_____
```

FIG. 3(a)

```
595  GGG ATG CCG CTT GGC AAA GAG GGC CCT TTT GTG CAT ATC GCA AGC ATG TGT GCT
199   G   M   P   L   G   K   E   G   P   F   V   H   I   A   S   M   C   A
     ─────────────────────────                          ───────────────────

649  GCC CTT CTC AGC AAG TTC CTC TCC CTC TTT GGG GGT ATC TAT GAG AAT GAA TCC
217   A   L   L   S   K   F   L   S   L   F   G   G   I   Y   E   N   E   S
                         ───────D4────────────────────────────────  +

703  CGG AAC ACA GAG ATG CTG GCT GCC GCC TGT GCC GTG GGG GTG GGC TGC TGC TTC
235   R   N   T   E   M   L   A   A   A   C   A   V   G   V   G   C   C   F
                             ─────────────────────────────────────────D5───

757  GCG GCA CCT ATT GGA GGC GTC CTC TTC AGC ATC GAG GTC ACC TCC ACC TTC TTT
253   A   A   P   I   G   G   V   L   F   S   I   E   V   T   S   T   F   F
     ─────────────

811  GCA GTG CGG AAC TAC TGG CGG GGC TTC TTC GCT GCC ACC TTC AGT GCC TTC ATC
271   A   V   R   N   Y   W   R   G   F   F   A   A   T   F   S   A   F   I
                                                             ──D6──────────

865  TTC CGG GTC TTG GCA GTC TGG AAC CGG GAT GAA GAG ACT ATT ACA GCC CTC TTC
289   F   R   V   L   A   V   W   N   R   D   E   E   T   I   T   A   L   F
     ──────────────────────────────

919  AAA ACC CGA TTC CGG CTC GAC TTC CCC TTT GAC CTG CAG GAG CTG CCA GCC TTT
307   K   T   R   F   R   L   D   F   P   F   D   L   Q   E   L   P   A   F
                                                     ──────────────────────

973  GCT GTC ATT GGT ATT GCT AGT GGC TTC GGT GGA GCC CTC TTT GTC TAC CTG AAC
325   A   V   I   G   I   A   S   G   F   G   G   A   L   F   V   Y   L   N
     ───────────────────────────────────D7──────────────────────────────────

1027 CGG AAG ATT GTC CAG GTG ATG CGG AAG CAG AAA ACC ATC AAT CGC TTC CTC ATG
343   R   K   I   V   Q   V   M   R   K   Q   K   T   I   N   R   F   L   M

1081 AGG AAA CGC CTG CTC TTC CCG GCT CTG GTG ACC CTG CTC ATC TCC ACG CTG ACC
361   R   K   R   L   L   F   P   A   L   V   T   L   L   I   S   T   L   T
      K                ─────────────────────────────────────D8──────────────

1135 TTC CCC CCT GGC TTT GGA CAG TTC ATG GCT GGA CAG CTC TCA CAG AAA GAG ACG
379   F   P   P   G   F   G   Q   F   M   A   G   Q   L   S   Q   K   E   T
     ──────────────────────                              #

1189 CTG GTC ACC CTG TTT GAC AAT CGG ACG TGG GTC CGC CAG GGC CTG GTG GAG GAG
397   L   V   T   L   F   D   N   R   T   W   V   R   Q   G   L   V   E   E
                         +                                              D

1243 CTA GAA CCA CCC AGC ACC TCA CAG GCC TGG AAC CCA CCA CGT GCC AAC GTC TTC
415   L   E   P   P   S   T   S   Q   A   W   N   P   P   R   A   N   V   F
          G   A                              S                            ─

1297 CTC ACC CTG GTC ATC TTC ATT CTC ATG AAG TTC TGG ATG TCT GCA CTG GCC ACC
433   L   T   L   V   I   F   I   L   M   K   F   W   M   S   A   L   A   T
                                         ────D9────────────────────────────
```

FIG. 3(b)

```
1351  ACC ATC CCA GTT CCC TGT GGG GCC TTC ATG CCT GTC TTT GTC ATT GGA GCA GCA
451    T   I   P   V   P   C   G   A   F   M   P   V   F   V   I   G   A   A
                                                                  _____D10_____

1405  TTT GGG CGT CTG GTG GGT GAA AGC ATG GCT GCC TGG TTC CCA GAT GGA ATT CAT
469    F   G   R   L   V   G   E   S   M   A   A   W   F   P   D   G   I   H
       _____

1459  ACG GAC AGC AGC ACC TAC CGG ATT GTG CCT GGG GGC TAC GCT GTG GTC GGG GCA
487    T   D   S   S   T   Y   R   I   V   P   G   G   Y   A   V   V   G   A
                       #             _____D11__

1513  GCT GCG CTG GCA GGA GCG GTG ACA CAC ACA GTG TCC ACG GCT GTG ATC GTG TTC
505    A   A   L   A   G   A   V   T   H   T   V   S   T   A   V   I   V   F
       _____

1567  GAG CTC ACA GGC CAG ATT GCC CAC ATC CTG CCT GTC ATG ATC GCC GTC ATC CTG
523    E   L   T   G   Q   I   A   H   I   L   P   V   M   I   A   V   I   L
                               _____D12_____

1621  GCC AAC GCT GTC GCC CAG AGT CTG CAG CCC TCC CTC TAT GAC AGC ATC ATC CGA
541    A   N   A   V   A   Q   S   L   Q   P   S   L   Y   D   S   I   I   R

1675  ATC AAG AAA CTG CCC TAC CTG CCT GAG CTC GGC TGG GGC CGC CAC CAG CAG TAC
559    I   K   K   L   P   Y   L   P   E   L   G   W   G   R   H   Q   Q   Y

1729  CGG GTG CGT GTG GAG GAC ATC ATG GTG CGG GAT GTT CCC CAT GTG GCC CTC AGC
577    R   V   R   V   E   D   I   M   V   R   D   V   P   H   V   A   L   S

1783  TGC ACC TTC CGG GAC CTG CGT TTG GCA CTG CAC AGG ACC AAG GGC CGA ATG CTG
595    C   T   F   R   D   L   R   L   A   L   H   R   T   K   G   R   M   L
           #

1837  GCC CTA GTG GAG TCC CCT GAG TCC ATG ATT CTG CTG GGC TCC ATC GAG CGT TCA
613    A   L   V   E   S   P   E   S   M   I   L   L   G   S   I   E   R   S

1891  CAG GTG GTG GCA TTG TTG GGG GCC CAG CTG AGC CCA GCC CGC GGC CGG CAG CAC
631    Q   V   V   A   L   L   G   A   Q   L   S   P   A   R   R   R   Q   H

1945  ATG CAG GAG CGC AGA GCC ACC CAG ACC TCT CCA CTA TCT GAT CAG GAG GGT CCC
649    M   Q   E   R   R   A   T*  Q   T   S   P   L   S   D   Q   E   G   P
                       K   L       K   A       M           P                   S

1999  CCT AGC CCT GAG GCT TCT GTC TGC TTC CAG GTG AAC ACA GAA GAC TCA GCC TTC
667    P   S   P   E   A   S   V   C   F   Q   V   N   T   E   D   S   A   F
                   S           T       I   R                               G
```

FIG. 3(c)

| | | | | | | | | | | | | | | | | | | |
|---|---|---|---|---|---|---|---|---|---|---|---|---|---|---|---|---|---|---|
| 2053 | CCA | GCA | GCC | CGG | GGG | GAG | ACC | CAC | AAG | CCC | CTA | AAG | CCT | GCA | CTC | AAG | AGG | GGG |
| 685 | P | A | A | R | G | E | T | H | K | P | L | K | P | A | L | K | R | G |
| | G | | H | | | Q | | | | | | | | | | | | |

| | | | | | | | | | | | | | | | | | | |
|---|---|---|---|---|---|---|---|---|---|---|---|---|---|---|---|---|---|---|
| 2107 | CCC | AGT | GTC | ACC | AGG | AAC | CTC | GGA | GAG | AGT | CCC | ACA | GGG | AGC | GCA | GAG | TCG | GCA |
| 703 | P | S | V | T | R | N | L | G | E | S | P | T | G | S | A | E | S | A |
| | | | N | A | T | S | | Q | | G | T | | | | N | M | | |

| | | | | | | | | | | | | | | | | | | |
|---|---|---|---|---|---|---|---|---|---|---|---|---|---|---|---|---|---|---|
| 2161 | GGC | ATC | GCC | CTC | CGG | AGC | CTC | TTC | TGT | GGC | AGT | CCA | CCC | CCT | GAG | GCT | GCT | TCG |
| 721 | G | I | A | L | R | S | L | F | C | G | S | P | P | P | E | A | A | S |
| | | | | | | | | | | | | L | | S | | T | T | # |

| | | | | | | | | | | | | | | | | | | |
|---|---|---|---|---|---|---|---|---|---|---|---|---|---|---|---|---|---|---|
| 2215 | GAG | AAG | TTG | GAA | TCC | TGT | GAG | AAG | CGC | AAG | CTG | AAG | CGT | GTC | CGA | ATC | TCC | CTG |
| 739 | E | K | L | E | S | C | E | K | R | K | L | K | R | V | R | I | S | L |
| | | | S | | | | D | | | | | | | | | | | |

| | | | | | | | | | | | | | | | | | | |
|---|---|---|---|---|---|---|---|---|---|---|---|---|---|---|---|---|---|---|
| 2269 | GCA | AGT | GAC | GCG | GAC | CTG | GAA | GGC | GAG | ATG | AGC | CCT | GAA | GAG | ATT | CTG | GAG | TGG |
| 757 | A | S | D | A | D | L | E | G | E | M | S | P | E | E | I | L | E | W |
| | | | | S | | | | | K | | | | | | | | | |

| | | | | | | | | | | | | | | | | | | |
|---|---|---|---|---|---|---|---|---|---|---|---|---|---|---|---|---|---|---|
| 2323 | GAG | GAG | CAG | CAA | CTA | GAT | GAA | CCT | GTC | AAC | TTC | AGT | GAC | TGC | AAA | ATT | GAT | CCT |
| 775 | E | E | Q | Q | L | D | E | P | V | N | F | S | D | C | K | I | D | P |
| | | | | | | | | | | + | | | | | | | | |

| | | | | | | | | | | | | | | | | | | |
|---|---|---|---|---|---|---|---|---|---|---|---|---|---|---|---|---|---|---|
| 2377 | GCT | CCC | TTC | CAG | CTG | GTG | GAG | CGG | ACC | TCT | TTG | CAC | AAG | ACT | CAC | ACT | ATC | TTC |
| 793 | A | P | F | Q | L | V | E | R | T | S | L | H | K | T | H | T | I | F |

| | | | | | | | | | | | | | | | | | | |
|---|---|---|---|---|---|---|---|---|---|---|---|---|---|---|---|---|---|---|
| 2431 | TCA | CTG | CTG | GGA | GTG | GAC | CAT | GCT | TAT | GTC | ACC | AGT | ATT | GGC | AGA | CTC | ATT | GGA |
| 811 | S | L | L | G | V | D | H | A | Y | V | T | S | I | G | R | L | I | G |
| | | | | | | | | | D13 | | | | | | | | | |

| | | | | | | | | | | | | | | | | | | |
|---|---|---|---|---|---|---|---|---|---|---|---|---|---|---|---|---|---|---|
| 2485 | ATC | GTT | ACT | CTA | AAG | GAG | CTC | CGG | AAG | GCC | ATC | GAG | GGC | TCT | GTC | ACA | GCA | CAG |
| 829 | I | V | T | L | K | E | L | R | K | A | I | E | G | S | V | T | A | Q |
| | | | # | | | | | | | | | | | | | | | |

| | | | | | | | | | | | | | | | | | | |
|---|---|---|---|---|---|---|---|---|---|---|---|---|---|---|---|---|---|---|
| 2539 | GGT | GTG | AAA | GTC | CGG | CCG | CCC | CTC | GCC | AGC | TTC | CGA | GAC | AGT | GCC | ACC | AGC | AGC |
| 847 | G | V | K | V | R | P | P | L | A | S | F | R | D | S | A | T | S | S |
| | | | | | | | | | | # | | | | | | | | |

| | | | | | | | | | | | | | | | | | | |
|---|---|---|---|---|---|---|---|---|---|---|---|---|---|---|---|---|---|---|
| 2593 | AGT | GAC | ACG | GAG | ACC | ACT | GAG | GTG | CAT | GCA | CTC | TGG | GGG | CCC | CAC | TCC | CGT | CAT |
| 865 | S | D | T | E | T | T | E | V | H | A | L | W | G | P | H | S | R | H |
| | | | | | | | | | | | | | | | | | | R |

| | | | | | | | | | | | | | | | | | |
|---|---|---|---|---|---|---|---|---|---|---|---|---|---|---|---|---|---|
| 2647 | GGC | CTC | CCC | CGG | GAG | GGC | AGC | CCT | TCC | GAC | AGC | GAC | GAC | AAA | TGC | CAA | TGA |
| 883 | G | L | P | R | E | G | S | P | S | D | S | D | D | K | C | Q | - |
| | | | | | | T | | | | | | | | | | | |

```
2698 gcccctcgtgggtggcctaggatggtgctagccatgcccgtcagcccagaatgtgcatctttcattccttct
2777 gccttcggaaggcaggaggcagctacagctggaggctgcaccccagccccctccagacctggggtgccagct
2842 tctcccagttcatcctacctggaatctgacccactacccacctgcaacaagtcttccagaggcaggaagata
2914 ggccctgccctggcaggatgggttggggtcacttgacccctgctcccccttcgaggggaaggggtggaact
2986 aagatggggtttataactggaacctccaatgaccagactgtatatagagatttacaaagatttttatattaat
3058 ttaataaacaaattcttaaatagaacaaaataaacacctaatgagccactttatatataaaaaaaaaaaa
3130 aaaa.
```

FIG. 3(d)

CHEMICAL MODIFICATION OF CHLORIDE CHANNELS AS A TREATMENT FOR CYSTIC FIBROSIS AND OTHER DISEASES

This application claims the benefit of U.S. Provisional Application Ser. No. 60/018,725, fled May 31, 1996.

The research underlying this invention has been supported by one or more of the following grants: CFF RDP R457 to Children's Hospital, Cincinnati, Ohio, NIH DK 43816, NIH DK 43377, and NIH 1P01 51832.

BACKGROUND OF THE INVENTION

This invention relates generally to medical treatment methods. Specifically, the invention relates to methodology for the correction of defective chloride transport by activation of chloride channels of the lung and other epithelia using genetic or chemical modification. These methods relate to the treatment of epithelia with compounds which cause activation of the channel as measured by increased probability (Po) of opening of the channel at physiologically relevant holding potentials. These methods also relate to the treatment of epithelia with gene therapy to introduce chloride channels genes with site mutations which cause activation of the channel as measured by increased probability (Po) of opening of the channel at physiologically relevant holding potentials. These treatments will reduce life-threatening complications frequently found in diseases such as cystic fibrosis. These methods of activation of chloride channels also comprise treatment of chloride channels with amidation reactions.

Cystic fibrosis is a lethal disease affecting approximately one in 2,500 live Caucasian births and is the most common autosomal recessive disease in Caucasians. Patients with this disease have reduce chloride ion permeability in the secretory and absorptive cells of organs with epithelial cell linings, including the airways, pancreas, intestine, sweat glands and male genital tract. This, in turn, reduces the transport of water across the epithelia. The lungs and the GI tract are the predominant organ systems affected in this disease and the pathology is characterized by blocking of the respiratory and GI tracts with viscous mucus. The chloride impermeability in affected tissues is due to mutations in a specific chloride channel, the cystic fibrosis transmembrane conductance regulator protein (CFTR), which prevents normal passage of chloride ions through the cell membrane (Welsh et al., Neuron, 8:821–829 (1992)). There is no effective treatment for the disease, and therapeutic research is focused on gene therapy and/or activating the defective or other chloride channels in the cell membrane to normalize chloride permeability (Tizzano et al., *J. Pediat.*, 120:337–349 (1992)). Damage to the lungs due to mucus blockage, frequent bacterial infections and inflammation is the primary cause of morbidity and mortality in CF patients and, although maintenance therapy has improved the quality of patients' lives, the median age at death is still only around 30 years.

The thick build-up of mucus deposits in the lungs leads to a higher than normal susceptibility towards fatal pulmonary infections. It is these infections, often of the *Pseudomonas aeruginosa* type, that are generally the causative agents of cystic fibrosis related death. At present, the established treatment protocols for cystic fibrosis involve treating these secondary infections with appropriate antibiotics, as well as adjusting diet and removing by physical means the deleterious build up of mucociliary secretions. Thus considerable current effort is being devoted to developing treatments that operate by attacking the underlying cause of disease. Here, a variety of approaches have been explored. These range from attempts at gene therapy (incorporating the normal, wild-type cystic fibrosis gene into epithelia cells) to the administration of agents that restore electrolyte balance either by opening up other non-CFTR dependent chloride anion channels or by inhibiting cellular uptake of sodium cations. Unfortunately, the viability of this latter electrolyte balance restoration approach still remains limited.

Gene replacement therapy approaches have been successful in treating genetic diseases including adenosine deaminase deficiency, and gene therapy holds great promise in providing a cure for a variety of other genetic diseases, including cystic fibrosis. Transfection of a wide variety of cells, including human pancreatic adenocarcinoma (CFPAC) cells with the cDNA encoding normal CFTR increases transport of chloride exhibited by those cells. These studies suggest that transfection of human lung epithelia with CFTR cDNA might lead to a treatment for cystic fibrosis. Indeed, a number of past and current studies to evaluate the safety and efficacy of transfer of the CFTR to the respiratory epithelia of human cystic fibrosis patients using adenoviral and other transfer vectors have appeared or are in progress. However, such approaches may be expensive and may have associated side effects such as inflammation which must be overcome before gene therapy can become an effective routine treatment regimen for cystic fibrosis.

The activation of the defective and/or alternative functioning chloride channels in cystic fibrosis epithelial cells in order to normalize their permeability to chloride is one of the primary therapeutic goals of the treatment of cystic fibrosis and has not yet been accomplished (Boat, T. F., Welsh, M. J. and Beaudet, A. L., "Cystic Fibrosis" in *The Metabolic Basis of Inherited Disease*, pp. 2649–2680 (Striver, C. R., Beaudet, A. L., Sly, W. S. and Valle, D. eds.) McGraw-Hill, New York (1989)). Thus, there exists an urgent need for a treatment that increases the permeability of epithelial cells to chloride and thereby can be used to treat cystic fibrosis. Such a treatment would be most beneficial if it were nontoxic and nonirritating to the epithelial cell linings, yet allowed the restoration of the proper chloride equilibrium of the cells, as well as the clearing of existing mucus. The present invention satisfies this need by providing methods and compounds which can therapeutically relieve both the cause of the manifestations of cystic fibrosis, as well as the manifestations themselves.

"ClC" Chloride Channels

ClC Chloride channels are widely distributed. The family of channels includes many types and many variants and isoforms of each type. They are widely distributed in nature and may play important, yet undiscovered roles in chloride transport. Indeed, the nature, role, and mechanisms of regulation of these channels and the processes they participate in are poorly understood. The following information provides a background information on ClC chloride channels.

The ClC chloride channels may play important, yet undiscovered roles in chloride transport in addition to the well known involvement in regulation of cellular volume, such as in the regulation of the resting potential of muscle membrane where defective channels lead to myotonia, and in kidney disease, where defective channels lead to Dent's disease.

The channel can be modeled as a central transmembrane region with an extracellular loop which contains the pH sensor, an N-terminal region which contains an inactivation region, and a C-terminal region which forms an activation region.

In normal mouse airway, the CFTR, a PKA-activated Cl-channel and the as yet unidentified $Ca^{2+}$ activated Cl-channel contribute the bulk of the Cl-current carried by the cells. Approximately 25% of the total current is carried by the CFTR, the remainder is carried by a $Ca^{2+}$ activated Cl-channels. Thus, the $Ca^{2+}$ activated Cl-channel is a major contributor to Cl-transport in the airway of the mouse, and is likely responsible for he mild disease phenotype in the CFTR (−/−) mouse lung. The molecular nature of this channel is not known, despite recent advances in determination of the primary sequence of a variety of other mammalian Cl-channels. In the case of genetic mutation of this protein in human cystic fibrosis patients, Cl-transport is defective in several organ systems including the lung, gut, and pancreas, and the defect is associated with disease. CaMKII-activated Cl-channels.

$Ca^{2+}$-activation of chloride channels in SV40 transformed cell lines from normal and CF airway epithelia is mediated by CaMKII. However, the molecular nature of this channel is unknown. Our findings have shown that ClC-2G chloride channels are activated by calmodulin kinase II ("CaMKII"). In addition, a chloride channel protein purified from bovine trachea has also been shown to be CaMKII-activated. Using antibodies raised to be bovine tracheal channel protein, a preliminary report suggested that a novel chloride channel (CaMKII-activated) had been cloned and that its structure was dissimilar to ClC channels and CFTR. However, full publication of structure of this channel has not yet appeared.

Framework for interpretation of $Ca^{2+}$-activation effects.

$Ca^{2+}$ clearly activates chloride channel activity in airway epithelium. To our knowledge, the mechanisms of $Ca^{2+}$ activation have not been examined in detail. Thus, increase in short-circuit current (SCC) attributable to increased chloride channel function with $Ca^{2+}$ in airway epithelia may equally be attributable to increased recruitment and increased probability opening of Cl channels, mechanisms which have not been addressed in detail in the literature, largely due to difficulties of dissociation of these two types of activation mechanisms unless single studies of Po of the $Ca^{2+}$-activated chloride channels are carried out in single channel studies (which have not appeared in the literature).

U.S. Pat. No. 5,242,947, Cherksey et al., issued Sep. 7, 1993, discloses methods for regulating cation transport across cellular membranes possessing cation channels. The cell membrane possessing a specific ion channel is exposed to a non-aromatic polyamine compound having a lysine- or arginine-based moiety (or a guanidine moiety) coupled to a straight chain polyamine.

U.S. Pat. No. 4,937,270, Hamilton et al., describes a method for making a water-insoluble biocompatible gel by activating HA with a carbondiimide then reacting the activated HA with a nucleophile (e.g., an amine).

U.S. Pat. No. 5,503,989, Bibbs et al., issued Apr. 2, 1996, discloses methods of preparing a peptide having a C-terminal amide group ("peptide amide") from the corresponding peptide having a C-terminal carboxyl group ("peptide acid"). Thus, a solution of peptide acid is treated with a carboxyl activating agent to give a reactive intermediate. Suitable carboxyl activating agents include carbodiimide compounds. The reactive intermediate is then treated with a trapping agent and an amine source (which is the donor —NH2) to give the peptide amide. According to a second, preferred, aspect of the invention, the peptide acid is treated with an alcohol in the presence of an acid to give a reactive intermediate different from that referred to above.

U.S. Pat. No. 5,504,241, Pohl et al., issued Apr. 2, 1996, discloses carbodiimides and/or oligomeric polycarbodiimides based on 1,3-bis(1-methyl-1-isocyanathoethyl)benzene, their preparation, and their use as hydrolysis stabilizers.

The carbodiimides have been used as stabilizers against hydrolytic cleavage of polyester-based plastics. See, e.g., U.S. Pat. No. 3,193,523.

U.S. Pat. No. 5,399,346, Anderson, issued Mar. 21, 1995, discloses the use of primary human cells which are genetically engineered with DNA (RNA) encoding a marker or therapeutic which is expressed to be expressed in vivo. Such engineered cells may be used in gene therapy.

U.S. Pat. No. 5,240,846, Collins et al, issued Aug. 31, 1993, discloses gene therapy for treating cystic fibrosis(CF). Delivery and expression of a single copy of a normal CFTR gene leads to stable correction of the Cl channel regulation defect present in CF epithelial cells. The present invention includes recombinant viral and plasmid vectors, alternative CFTR gene delivery strategies, and transduced CF cells and cell lines carrying a recombinant gene for functional CFTR. CF epithelial complementation through transduction of the present invention also provides an assay for determining the validity of other putative CF mutations. None of these references individually or collectively teach or suggest the present invention.

SUMMARY OF THE INVENTION

This invention relates generally to medical treatment methods. The present invention concerns methods for modification of chloride channels. Specifically, the invention relates to methodology for the correction of defective chloride transport by activation of chloride channels of the lung and other epithelia using genetic or chemical modification. This activation of the channel is measured by increased probability ("Po") of opening of the channel at physiologically relevant holding potentials.

This invention is to activate chloride channels of the lung and other cells by using chemical or genetic modification and other methods which neutralize the charge on amino acids of the ClC chloride channels. Preferably, the charged amino acids which are neutralized are on he extracytosolic surface of ClC chloride channels. Most preferably, the charged amino acids which are neutralized are on the extracytosolic surface of ClC chloride channels between domains 8 and 9. In a further embodiment, the amino acid residue which is neutralized is one or more amino acids selected from the group consisting of glutamine, aspartic acid, arginine, and lysine.

The present methods also include gene therapy which comprises the delivery of a gene for one of the functional ClC chloride channels to affected epithelial cells. The ClC gene of the present invention is any nucleic acid sequence which codes for one of the functional ClC chloride channels and may contain one or more site mutations in the nucleic acid sequence thereby encoding for an uncharged amino acid residue in place of a charged amino acid residue. Alternatively, a normal ClC gene may be used and the resulting encoded channel chemically modified to neutralize the charged amino acid residues.

The method of activation of chloride channels comprises administering to a patient in need of such treatment an activation amount of a composition comprising an amine and a condensation agent.

It is an object of the present invention to provide a method of increasing the permeability of epithelial cells to chloride ions in a subject comprising administering a permeability enhancing amount of a composition comprising a non-toxic, condensation agent and a non-toxic, amine.

It is also object of the present invention to provide a method for treating cystic fibrosis in a subject comprising administering a safe and pharmaceutically effective amount of a non-toxic, condensation agent and a safe and pharmaceutically effective amount of a non-toxic, amine.

BRIEF DESCRIPTION OF THE FIGURES

FIG. 1. Amino acid similarity comparison. Amino acid sequences of rabbit gastric ClC-2 (ClC-2G) (SEQ ID NO:1:) and rat brain ClC-2 (ClC-2) (SEQ ID NO:2:) are compared. Gaps were introduced into ClC-2G (asterisks) to maintain alignment. Dashes in ClC-2 indicate identity to corresponding residues in ClC-2G. Hydrophobic regions that are sufficiently hydrophobic to be considered as potential transmembrane domains are overlined and labeled D1–D13. Potential protein kinase A (PKA), calcium and phospholipid dependent kinase (PKC) and calcium and calmodulin kinase II (CaMKII) sites which are introduced into ClC-2G (not present in ClC-2) are indicated by arrows. The two potential PKC phosphorylation sites present in ClC-2 but removed from ClC-2G are indicated with dots above the residues. E419, which has been shown by site directed mutagenesis to be important to the pH sensor, is shown indicated by a double asterisk (**).

FIGS. 3(a through d). Nucleotide sequence (SEQ ID NO:3:) and resulting amino acid sequence (SEQ ID NO:4:) of human gastric ClC-2 (hClC-2G). Nucleotides are numbered +1 through +3133 from the first base of the putative initiator methionine. Amino acids are shown in single letter code, changes from rat ClC-2 are shown below the human sequence. Hydrophobic segments D1–D13 are shown by underlining; consensus sequences for phosphorylation by cAMP-dependent kinase A is indicated by ("*") and residues predicted to be phosphorylated by protein kinase C are designated by ("#"). Potential N-glycosylation sites are indicated by ("+"). The AATAAA (nt 3088-3093) polyadenylation signal is underlined.

DETAILED DESCRIPTION OF THE INVENTION

Figure 2:
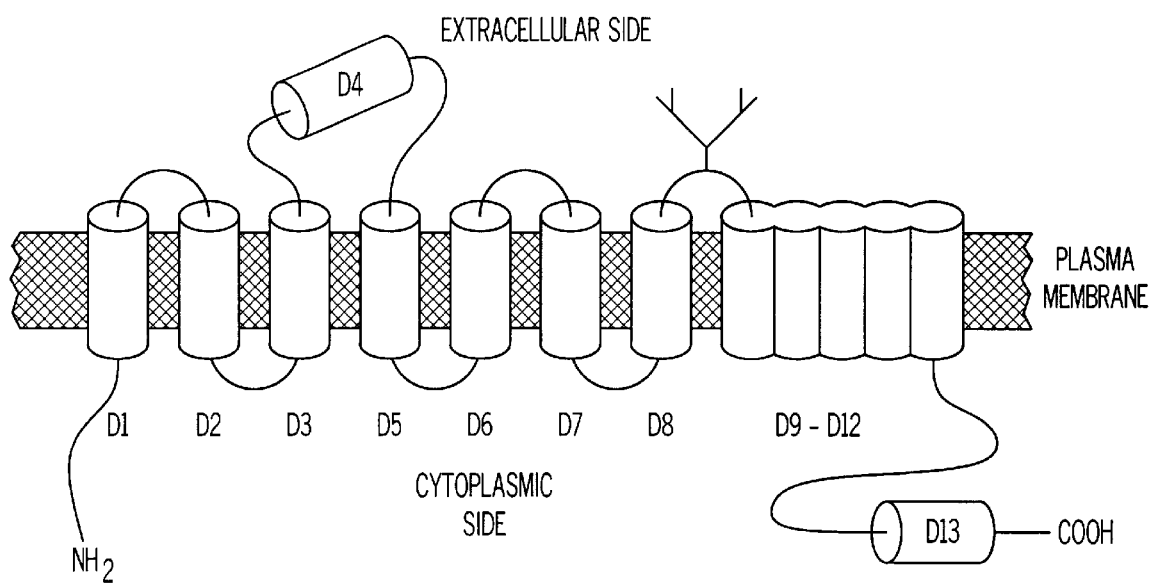
FIG. 2. Topology of ClC Chloride Channel Family. Chloride channels of the ClC family contain 12 putative membrane spanning domains (D1–D12). Both the amino terminal putative inactivating domain and the carboxyl terminal putative regulatory domain are cytoplasmic. The extracytosolic loop between D8 and D9 contains the putative pH sensor at residue 419.

Abbreviations for the amino acids residues are: A, Ala; C, Cys; D, Asp; E, Glu; F, Phe, G, Gly; H, His; I, Ile; K, Lys; L, Leu; M, Met; N, Asn; P, Pro; Q, Gln; R, Arg; S, Ser; T, Thr; V, Val; W, Trp; and Y, Try.

As used herein, the term "in vivo delivery" refers to delivery of a biologic by such routes of administration as oral, intravenous, subcutaneous, intraperitoneal, intrathecal, intramuscular, intracranial, inhalational, topical, transdermal, suppository (rectal), pessary (vaginal), and the like.

As used herein, the term "EDC" refers to water soluble carbodiimide 1-ethyl 3-(3-dimethylaminopropyl) carbodiimide.

As used herein, "a permeability enhancing amount" of a composition is that amount that causes the epithelial cell membrane to allow the passage of anions.

As used herein, "a safe and effective amount" of a composition is that amount which is pharmaceutically safe to a subject and that causes the epithelial cell membrane to allow the passage of anions while causing no or an acceptable level of side effects.

As used herein, "$[Ca^{2+}]$" refers to intracellular free calcium.

The present invention concerns methods for modification of chloride channels. Specifically, the methods comprise correction of defective chloride transport by activation of chloride channels of the lung and other epithelia. This invention describes the use of modification to activate chloride transport by the epithelia which cause activation of the channel as measured by increased probability ("Po") of opening of the channel at physiologically relevant holding potentials.

Since there are a large number of members of the ClC family in humans, and likely others to be yet discovered, these channels may be treated using the methods of the present invention, since they have highly conserved sequences and would be expected to behave similarly and give similar benefits with modulation of chloride transport.

ClC Chloride Channel Charge Neutralization

This invention is to activate chloride channels of the lung and other cells by using chemical or genetic modification and other methods which neutralize the charge on amino acids of the ClC chloride channels, preferably, the charged amino acids which are neutralized are on the extracytosolic surface of ClC chloride channels. Most preferably, the charged amino acids which are neutralized are on the extracytosolic surface of ClC chloride channels between domains 8 and 9.

In a further embodiment, the amino acid residue which is neutralized is one or more amino acids selected from the group consisting of glutamine, aspartic acid, arginine, and lysine.

The ClC family of chloride channels is widely distributed in the tissues, and is involved in many cellular processes including secretion, absorption and nerve and muscle function. Defective ClC-chloride channels have been shown to be responsible for several disease states, and activated ClC channels may be used to replace or partially substitute for other channels such as CFTR. Activation of ClC-chloride channels can be accomplished by any chemical or genetic modification of charged amino acid residues of members of the family of ClC chloride channels through application of such methods. An immediate application of these results might be in the lung, which contains ClC chloride channels, and where cystic fibrosis results from defective CFTR, a member of another class of chloride channel.

Activation of chloride transport may be used to treat disease states or where there is defective chloride transport or where it is desirable to activate chloride transport for other reasons. In one embodiment, amidation catalyzed by water soluble condensation agent such as a carbodiimide to activate chloride transport ClC-chloride channels is used. The amidation will thereby reduce the charge on one or more residues, causes activation of the channel as measured by increased probability (Po) of opening of the channel at physiologically relevant holding potentials.

In another embodiment, gene therapy can be used to introduce ClC chloride channels into epithelial cells. The ClC channels can contain one or more site mutation whereby one or more charged amino acids, coded for by the ClC gene, are replaced by noncharged residues. Preferably, the nucleotides coding for one or more charged amino acid on the extracytosolic surface of ClC chloride channels are replaced with nucleotides coding for a noncharged amino acid residue. More preferably, the charged amino acids which are replaced are on the extracytosolic surface of ClC chloride channels between domains 8 and 9. Most preferably, the nucleotides coding for one or more charged amino acid on the extracytosolic surface of ClC chloride channels are replaced with nucleotides coding for noncharged amino acid residue selected from the group consisting of glutamine, aspartic acid, arginine, and lysine.

Alternatively, a gene for a normal ClC channel can be introduced followed by chemical treatment to modify the charged residues to activate the channels.

The ClC family of chloride channels is a rapidly expanding family of voltage gated chloride channels, which differ in structure and electrophysiological characteristics from the CFTR. FIG. 1 shows a schematic diagram of the ClC family of chloride channels, as suggested by hydropathy analysis, glycosylation studies, and chimeric constructs. The forms known to date are set forth in Table I.

TABLE I

C1C CHLORIDE CHANNELS

| | |
|---|---|
| C1C-0 | *Torpedo marmorata* electric organ |
| C1C-1 | Predominantly skeletal muscle. Defect leads to myotonia. |
| C1C-K1 | Kidney |
| C1C-K2 | Kidney specific. |
| C1C-2 | All tissues of rat. Volume activated. |
| C1C-2G or α | Stomach, lung, brain and intestine of rabbit and human. PKA and CaMKII activated. |
| C1C-3 | Wide distribution, including vascular smooth muscle, brain and lung. |
| C1C-4 | Muscle, brain and heart (30). |
| C1C-5 | Implicated in Dent's disease. |
| C1C-6 | Recently isolated gene. Unknown distribution. |
| C1C-7 | Recently isolated gene. Unknown distribution. |

These channels are 24–55% homologous to each other, except for C1C-3 and C1C-4 which are highly homologous, and C1C-2G and C1C-2 which may be from the same gene product.

Although all members are voltage-gated, each member exhibits different electrophysiological characteristics. The channels have 12 putative transmembrane domains (D1–D12). The ion pore in this family of chloride channels has not yet been identified, although the cytosolic end of the pore has been suggested to be closed to the end of D12, where there is a highly conserved (throughout the whole ClC family) essential lysine which when mutated affects gating and ion conduction. In addition, it has been convincingly shown that the N-terminal end of the ClC chloride channels are involved in inactivation. None of these voltage-gated ClC chloride channels have previously been shown to be activated by protein kinases, although this is likely due to insufficient study, since all of these channels have potential phosphorylation sites. No studies of chemical activation have been carried out.

In FIG. 1 is shown the amino acid sequence of rabbit stomach ClC-2G, a recombinant protein which is thought to be involved in the provision of chloride in gastric HCl secretion by the gastric parietal cell of rabbit stomach, and it, or similar forms, may be involved in secretion or absorption in other tissues and in other species. The sequence is that deduced from a clone (GeneBank accession number U15652) from rabbit stomach. It is shown in comparison with the sequence from rat brain sequence of ClC-2.

ClC-2G from the stomach and lung have been shown to be acid activated. A consistent feature of these ClC-2 channels is the presence of an putative inactivation domain in the N-terminal region, and a putative regulatory domain with potential sites for regulation by protein kinases. In the case of the ClC-2G, these sites have been shown to be involved in kinase-dependent regulation. The location of the pore of the channel is not known with certainty, but it is suggested to be near the C-terminal transmembrane region.

ClC-2G exhibits dramatic pH activation, such that the reduction of pH greatly increase Po with pK for the effect of approximately 4.0. E419, in the extracellular loop between D8 and D9, is likely to be responsible for this effect, and the structural basis for activation by pH, site directed mutagenesis and chemical modification. While the dramatic effect of acid is in activation of the channel is easily understood in terms of the physiology of the gastric parietal cell, the role of acid activation for the same channel in the lung and whether acid activation plays a role other tissue where this channel remains to be explained. Structural models for the action of this "pH sensor" including electrostatic interaction with other residues near the mouth of the pore will be explored.

Shown in FIG. 2 is the proposed topology of ClC chloride channels, deduced from hydropathy analysis and consistent with the results of glycosylation studies. Inspection of FIG. 2 and the sequence of ClC-2G shows a variety of carboxylic acid residues which may be involved in pH and chemical modification-dependent activation. For example, E169, E181, E208, E234, E236, D301, E302, and so on. Any of these residues, as well as tyrosines such as Y495 are possible targets of chemical modification. A preferable residue for modification is E(41( ). In ClC 2, this residue is a glycine.

E419 is present in the 43 amino acid stretch between proposed transmembrane segments D8 and D9. This loop contains 4 glutamic acids and an aspartic acid. E419 forms part of a glutamic acid rich locus, E416ELE. The only positive charges present on the outer surface of the channel are R127, K207, R300, R310, K314, K396, R406 and R410.

The ClC family of Cl-channels is a rapidly expanding family of voltage gated Cl channels, which differ in structure and electrophysiological characteristics from the CFTR. ClC—O was cloned from the *Torepdo marmorata* electric organ, ClC-1 is predominantly expressed in skeletal muscle and ClC-K1 and -K2 are kidney specific. Recently, it has been shown that Dent's disease, an X-lined renal tubular disorder, may result from a deletion of about 500 bp in ClC-K2. ClC-2, cloned from rat brain was suggested to be a ubiquitous Cl-channel involved in volume regulation in epithelial and non-epithelial tissues. ClC-3 cloned from rat kidney but predominantly expressed in rat brain was first thought to be inhibited by protein kinase C (PKC), but subsequently was shown to be inhibited only by $Ca^{2+}$ with no involvement of PKC. The human gene for ClC-4 was cloned and found by Northern analysis to be highly expressed in skeletal muscle brain and heart. However no functional studies on ClC-4 have been performed. Except for ClC-4 which has significant homology with ClC-3, these channel proteins are only 24–55% homologous with each other, but all have structural similarity with 12 putative transmembrane domains (D1–D12). Glycosylation studies suggest that D4 is extracytosolic and D9 to D12 is a broad hydrophobic region, the exact topology of which is unclear. Although all members are voltage-gated, each member exhibits different electrophysiological characteristics. The ion pore in this family of Cl-channels has not yet been identified, although the cytosolic end of the pore has been suggested to be close to the end of D12, where there is a highly conserved (throughout the whole ClC family) essential lysine which when mutated affects gating and ion conduction. None of these voltage-gated ClC Cl-channels except ClC-2G have previously been shown to be activated by protein kinases or by chemical modification.

In a preferred embodiment, the ClC gene comprises a functional, human ClC-2G gene, the sequence of which is shown in FIG. 3. The ClC-2G channels can contain one or more site mutation whereby one or more charged amino acids, coded for by the ClC-2G gene, are replaced by noncharged residues. Preferably, the nucleotides coding for one or more charged amino acid on the extracytosolic surface of ClC chloride channels are replaced with nucleotides coding for a noncharged amino acid residue. More preferably, the charged amino acids which are replaced are on the extracytosolic surface of ClC chloride channels between domains 8 and 9. Most preferably, the nucleotides coding for one or more charged amino acid on the extracytosolic surface of ClC chloride channels are replaced with nucleotides coding for a noncharged amino acid residue selected from the group consisting of glutamine, aspartic acid, arginine, and lysine.

ClC Chloride Channel Gene Therapy

The present methods also include gene therapy which comprises the delivery of a gene for one of the functional ClC chloride channels to affected epithelial cells. Delivery and expression of a single copy of one of the ClC chloride channels gene alleviates the chloride transport defect present in certain cells. Cystic fibrosis ("CF"), caused by a lack of functional CFTR or presence of CFTR function below physiologically-acceptable levels which arises from a defect in the CFTR gene, can thus be treated in accordance with the principles of the present invention. The "normal ClC gene" of the present invention is simply any nucleic acid sequence which codes for one of the functional ClC chloride channels. Thus variations in the actual sequence of the gene can be tolerated provided that functional ClC can be expressed. For example, silent mutations can be introduced to stabilized cloning of the gene. A ClC gene used in the practice of the present invention can be obtained through conventional methods such as DNA cloning, artificial construction or other means. The "mutated ClC gene" of the present invention is simply any nucleic acid sequence which codes for one of the functional ClC chloride channels and contains one or more site mutations in the nucleic acid sequence thereby encoding for an uncharged amino acid residue in place of a charged amino acid residue.

Gene transfer of the ClC gene in accordance with the present invention can be accomplished through a variety of means well known and standard in the art, including transfection using calcium phosphate co-precipitation, fusion of the target cell with liposomes, erythrocyte ghosts or spheroplasts carrying the ClC gene, plasmid and viral vector-mediated transfer and DNA protein complex-mediated gene transfer. Suitable gene therapy methods are well known in the art and are detailed in U.S. Pat. No. 5,399,346, Anderson, issued Mar. 21, 1995, and U.S. Pat. No. 5,240,846, Collins et al., issued Aug. 31, 1993, and are hereby incorporated in their entirety by reference.

Presently the delivery vehicle of choice is a recombinant retrovirus capable of infecting human epithelial cells. The recombinant retroviral vector of the invention generally comprises DNA of at least the portion of the retroviral genome necessary for infection, and the ClC gene operatively linked thereto. Additionally, the portion of retroviral genome used in construction of the vector can be rendered replication-defective to remove any deleterious effects of viral replication on the target cells.

Although any CF-affected epithelial cells such as pancreatic and sweat gland cells can be targeted with the gene transfer methods and vectors of the present invention, because the most severe complications of CF are usually pulmonary, airway epithelial cells are the most desirable targets for gene therapy of the present invention. Moreover, given that airway epithelial cells have been found to be easily infected by recombinant retroviruses, gene transfer in accordance with the present invention to these cells is quite feasible.

The present invention is thus directed towards gene therapy for cystic fibrosis and other diseases resulting from impaired chloride transport through delivery and expression of a functional ClC gene to the cells of a patient. Recombinant retroviral vectors as well as other ClC gene transfer schemes can be used in the practice of the present invention. The present invention further includes both CF epithelial cells and cell lines which carry a normal ClC gene transducted or transferred therein in accordance with the principles of the invention.

The cells targeted for transduction or gene transfer in accordance with the present invention include any cells to which the delivery of the ClC gene is desired. Generally speaking, the cells are those with the ClC gene defect, such as CF cells. In the case of CF, the cells targeted are preferably epithelial cells, including pancreatic, sweat gland, liver, intestinal, kidney and even more preferably epithelial airway cells, such as lung cells.

Cells or cell populations can be treated in accordance with the present invention in vivo or in vitro. For example, in in vivo treatments, ClC vectors of the present invention can be administered to the patient, preferably in a biologically compatible solution or pharmaceutically acceptable delivery vehicle, by ingestion, injection, inhalation or any other number of other methods. The dosages administered will vary from patient to patient and will be determined by the level of enhancement of ClC function balanced against any risk or deleterious side effects. Monitoring levels of transduction, ClC expression and/or the presence or levels of normal ClC will assist in selecting and adjusting the dosages administered. In vitro transduction is also contemplated within the present invention. Cell populations with defective ClC genes can be removed from the patient or otherwise provided, transduced with a normal or site mutated ClC gene in accordance with the principles of the invention, then (re)introduced into the patient.

One approach to the use of recombinant retroviruses and the treatment of CF or other diseases is to introduce a functional ClC gene into epithelial cells in vivo by directly delivery retroviruses to the effected tissue such as the airway. Several approaches can be taken for the direct delivery of retroviruses. The more invasive approach would be to intubate the patient and lavage the airway with concentrated solutions of ClC expressing retrovirus. Stable retroviral expression requires that the provirus integrates into chromosomal DNA. This occurs most efficiently if the recipient cells are dividing. It may be necessary to stimulate regeneration of the epithelial soon after exposure to virus. This could be accomplished with mechanical or chemical irritation of the airway.

The less invasive approach would be to deliver the normal ClC gene to airway epithelial cells in vivo by a nebulized preparation that can be inhaled. Many different pharmacologic agents are efficiently delivered to a large surface of the airway by nebulized treatments. It is possible that the beneficial effect achieved by this method may be transient. It may, therefore, be necessary to give repeated doses of the drug. The gene delivery system used for direct gene introduction may not have to be viral based. Direct inhalation of DNA protein complexes or DNA expression vectors in liposomes may be a safer and more effective gene delivery system than retroviruses.

Another method is the transplantation of genetically modified airway epithelial cells into a patient. This approach to somatic gene therapy of CF is similar in concept to bone marrow directed gene therapy. Airway epithelial cells are isolated from the CF patient, cultures of the cells are established, recombinant retroviruses are used to stably introduce the ClC gene in the cells, and the genetically modified cells are transplanted into the patient so they can re-populate the airway. In order to achieve efficient re-population in the airway with genetically modified cells, it may be necessary to perturb the integrity of the endogenous epithelial lining through mechanical or chemical irritation.

Amidation of the ClC Chloride Channels

This invention also relates to methods for the correction of defective chloride transport by activation of chloride channels of the lung and other epithelia using chemical modification by amidation. This method provides for the treatment of epithelia with amidation reaction compounds which cause activation of the channel as measured by increased probability (Po) of opening of the channel at physiologically relevant holding potentials. The amidation methods of the present invention comprise administering to epithelial cells in need of such treatment: (a) an amine compound and (b) a condensation agent.

This invention describes the use of amidation catalyzed by water soluble condensation agent such as a carbodiimide to activate chloride transport ClC-chloride channels. Activation of chloride transport may be used to treat disease states or where there is defective choloride transport or where it is desirable to activate choloride transport for other reasons. The methods of the present invention will preferably use a water soluble carbodiimide, e.g., 1-ethyl 3 (3-Dimethylaminopropyl)carbodiimide hydrochloride ("EDC") and glycine methyl ester to amidate the channel and thereby reduce the negative charge on one or more residues, causing activation of the channel as measured by increased probability (Po) of opening of the channel at physiologically relevant holding potentials.

The compounds of this invention are particularly contemplated for use in facilitating chloride anion exit and entry from cells. They will thus find use in the treatment of a variety of diseases and cystic fibrosis.

Glycine methyl ester may be used, buy many amines can substitute to give uncharged or more positively charge products. Other condensation agents, such as other carbodiimides, can also be used, and there are many modifications of the conditions and other compounds which are known to speed and stabilize the reactions with carbodiimides. Other reactions are known which result in similar products with carboxyl groups and other charged groups of proteins. Any of these which are sufficiently mild and which are safe could be used to alter the charge of the extracellular face of the channel.

A suitable condensation agent is, for example, a carbodiimide, such as diethyl- or dicyclohexyl-carbodiimide, N-ethyl-N-(dimethylaminopropyl) carbodiimide, N-ethyl-N-(dimethylamino) propylcarbodiimide hydrochloride, carbodiimide namely N-cyclohexyl-$N^1$-((2-morpholinyl)-ethyl)-carbodiimide-methyl-p-toluene sulfonate, carbonyldiimidazole, dicyclohexylcarbodiimide (DCC), 2-ethoxy-1-ethoxycarbonyl-1,2-dihydroquinolone (EEDQ), benzotriazol-1-yloxytris-(dimethylamino) phosphoniumhexafluorophosphate (BOP reagent), 2'-substituted aromatic and/or cycloaliphatic monocarbodiimides, e.g. 2,2', 6,6'-tetraisopropyldiphenylcarbodiimide, 2- and 2'-substituted aromatic and/or cycloaliphatic monocarbodiimides, e.g., 2,2;6,6'-tetraisoprophyldiphenl carbodiimide, dicylohexylcarbodiimide, 1-(3-dimethylaminoprophyl)-3-ethylcarbodiimide, diisopropylcarbodiimide, carbonyldiimidazole, dicychlohexylcarbodiimide and 1-ethyl 3-(3-dimethylaminoprophyl)carbodiimide hydrochloride. In a preferred embodiment, the reaction steps include providing an aqueous mixture of the carbodiimide as either a soluble monocarbodiimide or biscarbodiimide.

The appropriate amine may be an aliphatic, cycloaliphatic and/or araliphatic amines, alcohols and/or alkoxypolyoxyalkylene alcohols. In a preferred embodiment, the aliphatic, cycloaliphatic or araliphatic amines, alcohols and/or alkoxypolyoxyalkylene alcohols are preferably added to the condensation agent-containing reaction mixture but may be added separately, either before or after treatment with a condensation agent.

The amine may be optionally substituted with alkyl groups, aryl groups or aralkyl groups. The amine may be a primary, secondary, tertiary or quaternary amine. Suitable amines, for example primary or secondary amines, preferably have from about 1 to about 12 carbon atoms, preferably from about 2 to about 8 carbon atoms. Examples include methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine, ethylhexylamine, cyclohexylamine and benzylamine. The amine may be an amino acid, e.g., glycine, lysine, arginine, their derivatives and mixtures thereof or the amine may be a polyamine, e.g., putricine, spermidine, spermine, their derivatives or mixtures thereof. Preferred amines useful for the present method include ethanolamine, ethylenediamine, glucosamine, glycine methyl ester, glycine, lysine, arginine, their derivatives and mixtures thereof. Glycine methyl ester, glycine, arginine and lysine are preferred.

It is contemplated that such target cells may be located within an animal or human patient, in which case a safe and effective amount of the complex, in pharmacologically acceptable form, would be administered to the patient. Generally speaking, it is contemplated that useful pharmaceutical compositions of the present invention will include the selected condensation agent and amine in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

Any composition chosen should be of low or non-toxicity to the cell. Toxicity for any given compound may vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds which fit the criteria of the claims should also be considered when choosing a condensing reagent or amine. All of the compounds can be screened for efficacy following the methods taught in the examples.

The composition can comprise, in addition to the condensing reagent and amine, compounds and/or compositions that will also aid in relief of the symptoms of cystic fibrosis, such as a cyclic AMP agonist, a calcium ion agonist, human DNase 1, a sodium channel blocker or a pancreatic enzyme supplement, in dosages useful for relief of the symptoms of cystic fibrosis, as known to those skilled in the art. Cyclic AMP agonists can include, for example, forskolin and isoproterenol. Calcium ion agonists can include ionomycin, A23187, carbachol, bradykinin, duramycin and thapsigargin, for example. Sodium channel blockers can include amiloride and triamterene. Dosages for the above-mentioned additional compounds are established and known to those skilled in the art (see, e.g., Knowles et a., *New Eng. J Med* 322:1189–1194 (1990)).

Compositions for treating cystic fibrosis are provided which comprise a combination of a safe and effective amount of a suitable condensation agent and amine, as described above, a pharmaceutically-acceptable carrier, and a safe and effective amount of an agent selected from the group consisting of human DNase 1, cystic fibrosis transmembrane conductance regulator protein or a biologically active portion thereof, nucleic acid encoding functional cystic fibrosis transmembrane conductance regulator protein, a cyclic AMP agonist, a calcium agonist, a sodium channel blocker and a pancreatic enzyme supplement, as also described above. More than one agent can be added to the condensation agent and/or amine. The ratio of condensation agent to amine or additional agent is dependent upon the dose desired of each individual compounds. Preferably, the additional agent will be administered as a pharmaceutically-acceptable aqueous solution wherein the pharmaceutical composition comprises (1) from about 0.001% to about 10% of a condensation agent and amine, (2) from about 10% to about 99% of a pharmaceutically-acceptable carrier, and (3) from about 0.001% to about 10% of the additional agent or agents as described above.

Administration Methods

The compounds useful in the present inventive method may be administered by any suitable means. One skilled in the art will appreciate that many suitable methods of administering the compounds to an animal in the context of the present invention, in particular a human, are available, and, although more than one route may be used to administer a particular compounds, a particular route of administration may provide a more immediate and more effective reaction than another route.

The compounds may be administered directly to the lung of a patient Preferably, the compounds is administered as a pharmaceutically-acceptable aqueous solution or suspension. It is preferable that the compounds be administered as a pharmaceutically-acceptable aqueous solution containing from about 0.001% to about 10% (w/w) of the compounds. A pharmaceutically-acceptable aerosol is another preferred means of administration. The aerosol preferably contains from about 0.001% to about 10% (w/w) of the compounds. The compounds also may be administered orally. In such cases, the compounds will generally be administered in an amount of about 0.01 to about 10 mg/kg body weight. Other routes of administration, such as intravenous and intraperitoneal administration, are also possible.

The compounds should be administered such that a therapeutically effective concentration of the compounds is in contact with the affected cells of the body. The dose administered to an animal, particularly a human, in the context of the present invention should be sufficient to effect a therapeutic response in the animal over a reasonable period of time. The dose will be determined by the strength of the particular compounds employed and the condition of the animal, as well as the body weight of the animal to be treated. The size of the dose also will be determined by the existence, nature, and extent of any adverse side effects that might accompany the administration of a particular compounds and the particular route of administration employed with a particular patient. In general, the compounds of the present invention are therapeutically effective at low doses. The effective dose range is from about 0.01 mM to about 10 mM. Accordingly, the compounds will be generally administered in low doses.

The compounds may be administered in a pharmaceutically-acceptable carrier. Pharmaceutically-acceptable carriers are well-known to those who are skilled in the art. The choice of carrier will be determined in part by the particular compounds, as well as by the particular method used to administer the composition. Accordingly, there is a wide variety of suitable formulations of the pharmaceutical composition of the present invention.

Formulations suitable for oral administration include (a) liquid solutions, such as an effective amount of the compounds dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for administration by inhalation include aerosol formulations placed into pressurized acceptable propellants, such as dichlorodifluoromethane, trichlorofluoromethane, propane, nitrogen, and the like. The active agent may be aerosolized with suitable excipients. For inhalation administration, the composition can be dissolved or dispersed in liquid form, such as in water or saline, preferably at a concentration at which the composition is fully solubilized and at which a suitable dose can be administered within an inhalable volume. A suitable dose would place approximately 0.001 to about 5.0 mmol per liter of the composition on the airway surfaces approximately 4 times per day. Delivery can be repeated several times a day, depending upon the specific dosage chosen and the rate at which the chosen composition is cleared from the airways, with the goal being to maintain chloride permeability in the airway epithelial cells. Delivery may be through a nebulizer or a metered-dose inhaler.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, Higuchi, issued 1973, which is incorporated by reference herein.

The desirable extent of the induction of chloride efflux from cells will depend on the particular condition or disease being treated, as well as the stability of the patient and possible side effects. In proper doses and with suitable administration of certain compounds, the present invention provides for a wide range of activation of the rate of chloride ion efflux, e.g., from little activation to essentially full activation.

The present invention is expected to be effective in the treatment of all conditions, including diseases, that may be characterized by a reduced cellular apical chloride conductance. In particular, the present invention is expected to have utility in the treatment of chronic obstructive pulmonary diseases, in particular cystic fibrosis.

The exact amount of the compounds required will vary from subject to subject depending on the species, age, and general condition of the subject, the severity of the disease that is being treated, the particular compounds used, its mode of administration, and the like. Thus, it is not possible to specify an exact activity promoting amount However, an appropriate amount may be determined by one of ordinary skill in the art using only routine testing given the teachings herein.

EXAMPLES

The following examples illustrate the use of the process of this invention to activate the ClC chloride channels. The following examples illustrate and explain the present invention but are not to be taken as limiting the present invention in any regard.

Example 1
Mutant CDNA for the ClC Chloride Channel

A mutant for ClC is prepared using Transformer TM site-directed mutagenesis kit, according to the manufacturer's instructions. In this mutant, the channel MRNA is changed from GAA to GGA, creating a mutant channel with glycine in position 419, as it would appear in ClC-2. This mutant channel protein is shown to exhibit a high Po at pH 7.4 at physiologically relevant pH.

Site directed mutagenesis of glutamic acid (419) to glycine (GAA to GGA), also gives a channel with a high Po at neutral pH and physiologically relevant holding potentials. Site directed mutagenesis, reduction of pH and chemical modification of the channel at the extracytosolic surface all lead to activation of the chloride channel. These results all demonstrate that alteration of the actual or apparent charge on specific residues or regions of the extracellular face of the channel lead to activation of the channel at physiologically relevant pH of experienced by the channel in the tissues of interest.

Example 2
Treatment with Glycine Methyl Ester and EDC.

In this example, channel activation is by treatment of ClC-2G chloride channels with EDC plus glycine methyl ester using chloride channels reconstituted in planar lipid bilayers. The channels are treated with 20 mM glycine methyl ester and then 1 mM EDC. Activation is monitored by the addition of 30 nM recombinant chlorotoxin, a ClC-2G channel inhibitor. All additions are to the trans (extracytosolic) compartment. Media in both compartments contains 800 mM TEACl, 10 mM EGTA, 2 mM $MgCl_2$, 1 mM ATP, and 10 mM PIPES, pH 7.4. This is a sided addition to the extracytosolic surface of the channel, the same surface which would be exposed when the channel was in the plasma membrane of cells. Activation results from covalent modification of carboxylic acid or tyrosine residues, adducts to the latter residue may be by hydroxylamine which are accessible from the extracytosolic face of ClC-2G chloride channels.

What is claimed is:

1. A method of treating a pathology having symptoms caused by inadequate chloride transport by defective ClC-2G chloride channels, comprising administering to an individual in need of such treatment 1) a condensation agent and 2) an amine in amounts effective to activate chloride transport by inactivating charged groups on amino acid residues of said channels, thereby counteracting said symptoms.

2. A method according to claim 1, wherein the condensation agent comprises a carbodiimide.

3. A method according to claim 1, wherein the condensation agent is selected from the group consisting of diethylcarbodiimide, dicyclohexylcarbodiimide, N-ethyl-N-(dimethylaminopropyl) carbodiimide, N-ethyl-N (dimethylamino) propylcarbodiimide hydrochloride, N-cyclohexyl-N'-((2-morpholinyl)-ethyl)-carbodiimide-methyl-p-toluene sulfonate, carbonyl-diimidazole, dicyclohexylcarbodiimide, 2-ethoxy-1-ethoxycarbonyl-1,2-dihydroquinolone, benzotriazol-1-yloxytris (dimethylamino)-phosphoniumhexafluorophosphate, 2,2', 6,6'-tetraisopropyl-diphenylcarbodiimide, 2,2', 6,6'-tetraisopropyldiphenylcarbodiimide, dicyclohexylcarbodiimide, carbonyldiimidazole, 1-(3-dimethylaminopropyl)-3-ethylcarbodiimide, diisopropylcarbodiimide, carbonyldiimidazole, dicychlohexylcarbodiimide, 1-ethyl 3-dimethylaminopropyl)carbodiimide hydrochloride and mixtures thereof.

4. A method according to claim 1, wherein the amine comprises a compound selected from the group consisting of primary amines having from about 1 to about 12 carbon atoms, secondary amines having from about 1 to about 12 carbon atoms, amino acids, polyamines and mixtures thereof.

5. A method according to claim 1, wherein the amine comprises a compound selected from the group consisting of methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine, ethylhexylamine, cyclohexylamine, benzylamine, glycine methyl ester, glycine, arginine, lysine, ethanolamine, ethylenediamine, glucosamine, putricine, spermidine, spermine and mixtures thereof.

6. A method according to claim 1, comprising administering to the individual the condensation agent and the amine in the form of a composition comprising, by weight:
   (a) from about 0.001% to about 10% of the condensation agent;
   (b) from about 0.001% to about 10% of the amine; and
   (c) from about 10% to about 99% of a carrier.

7. A method according to claim 6, wherein the carrier is phosphate buffered saline.

8. A method according to claim 6, wherein the condensation agent comprises 1-ethyl 3-(3-dimethylaminopropyl) carbodiimide hydrochloride and the amine comprises glycine methyl ester.

9. A method of treating cystic fibrosis by activating chloride transport by defective ClC-2G chloride channels, comprising administering to an individual in need of such treatment an effective amount of 1) a condensation agent and 2) an amine.

10. A method according to claim 9, further comprising administering to the individual an agent selected from the group consisting of amiloride, human DNase 1, cystic fibrosis transmembrane conductance regulator protein, a biologically active portion of cystic fibrosis transmembrane conductance regulator protein, nucleic acid encoding functional cystic fibrosis transmembrane conductance regulator protein, a cyclic AMP agonist, a calcium ion agonist, a pancreatic enzyme supplement and mixtures thereof.

11. A method according to claim 9, wherein the amine is selected from the group consisting of primary amines having from about 1 to about 12 carbon atoms, secondary amines having from about 1 to about 12 carbon atoms, amino acids, polyamines and mixtures thereof.

12. A method according to claim 9, wherein the amine is selected from the group consisting of methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine, ethylhexylamine, cyclohexylamine, benzylamine, glycine methyl ester, glycine, arginine, lysine, ethanolamine, ethylenediamine, glucosamine, putricine, spermidine, spermine and mixtures thereof.

13. A method according to claim 12, wherein the amine is selected from the group consisting of ethanolamine, ethylenediamine, glucosamine, glycine methyl ester, glycine, lysine, arginine, and mixtures thereof.

14. A method according to claim 9, wherein the condensation agent comprises a carbodiimide.

15. A method according to claim 9, wherein the condensation agent is selected from the group consisting of diethylcarbodiimide, dicyclohexylcarbodiimide, N-ethyl-N-(dimethylaminopropyl) carbodiimide, N-ethyl-N (dimethylamino) propylcarbodiimide hydrochloride, N-cyclohexyl-N'-((2-morpholinyl)-ethyl)-carbodiimide-methyl-p-toluene sulfonate, carbonyldiimidazole, dicyclohexylcarbodiimide, 2-ethoxy-1-ethoxycarbonyl-1,2-dihydroquinolone, benzotriazol-1-yloxytris (dimethylamino)-phosphoniumhexafluorophosphate, 2,2', 6,6-'tetraisopropyl-diphenylcarbodiimide, 2,2', 6,6'-tetraisopropyldiphenylcarbodiimide, dicyclohexylcarbodiimide, carbonyldiimidazole, 1-(3-dimethylaminopropyl)-3-ethylcarbodiimide, diisopropylcarbodiimide, carbonyldiimidazole, dicychlohexylcarbodiimide, 1-ethyl 3-(3-dimethylaminopropyl)carbodiimide hydrochloride and mixtures thereof.

16. A method according to claim 9, wherein the condensation agent comprises 1-ethyl 3-(3-dimethylaminopropyl) carbodiimide hydrochloride and the amine comprises glycine methyl ester.

17. A method according to claim 9, comprising administering to the individual the condensation agent and the amine in the form of a composition comprising, by weight:

(a) from about 0.001% to about 10% of the condensation agent;

(b) from about 0.001% to about 10% of the amine; and (c) from about 10% to about 99% of a carrier.

* * * * *

```
SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 898 amino acids
        (B) TYPE: amino acid
        (D) TOPOLOGY: linear (ii) MOLECULE TYPE: protein (ix) FEATURE:
        (A) NAME/KEY:Rabbit Gastric CIC-2

(xi) SEQUENCE DESCRIPTION:   SEQ ID NO:1:

Met    Ala    Ala    Pro    Ala    Ala    Ala    Ala    Val    Glu
                           5                                    10

Glu    Gly    Met    Glu    Pro    Arg    Ala    Leu    Gln    Tyr
                           15                                   20

Glu    Gln    Thr    Leu    Met    Tyr    Gly    Arg    Tyr    Thr
                           25                                   30
```

```
Gln  Asp  Leu  Gly  Ala  Phe  Ala  Lys  Glu  Glu
                    35                        40

Ala  Ala  Arg  Ile  Arg  Leu  Gly  Gly  Pro  Glu
                    45                        50

Pro  Trp  Arg  Ser  Pro  Pro  Ser  Pro  Arg  Thr
                    55                        60

Pro  Pro  Glu  Leu  Leu  Glu  Tyr  Gly  Gln  Ser
                    65                        70

Arg  Cys  Ala  Arg  Cys  Arg  Met  Cys  Ser  Val
                    75                        80

Arg  Cys  His  Lys  Phe  Leu  Val  Ser  Arg  Val
                    85                        90

Gly  Glu  Asp  Trp  Ile  Phe  Leu  Val  Leu  Leu
                    95                        100

Gly  Leu  Leu  Met  Ala  Leu  Val  Ser  Trp  Ala
                    105                       110

Met  Asp  Tyr  Ala  Ile  Ala  Ala  Cys  Leu  Gln
                    115                       120

Ala  Gln  Gln  Trp  Met  Ser  Arg  Gly  Leu  Asn
                    125                       130

Thr  Asn  Leu  Leu  Leu  Gln  Tyr  Leu  Ala  Trp
                    135                       140

Val  Thr  Tyr  Pro  Val  Val  Leu  Ile  Thr  Phe
                    145                       150

Ser  Ala  Gly  Phe  Thr  Gln  Ile  Leu  Ala  Pro
                    155                       160

Gln  Ala  Val  Gly  Ser  Gly  Ile  Pro  Glu  Met
                    165                       170

Lys  Thr  Ile  Leu  Arg  Gly  Val  Val  Leu  Lys
                    175                       180

Glu  Tyr  Leu  Thr  Leu  Lys  Thr  Phe  Val  Ala
                    185                       190

Lys  Val  Ile  Gly  Leu  Thr  Cys  Ala  Leu  Gly
                    195                       200

Ser  Gly  Met  Pro  Leu  Gly  Lys  Glu  Gly  Pro
                    205                       210

Phe  Val  His  Ile  Ala  Ser  Met  Cys  Ala  Ala
                    215                       220

Leu  Leu  Ser  Lys  Phe  Leu  Ser  Leu  Phe  Gly
                    225                       230

Gly  Ile  Tyr  Glu  Asn  Glu  Ser  Arg  Asn  Thr
                    235                       240

Glu  Met  Leu  Ala  Ala  Ala  Cys  Ala  Val  Gly
                    245                       250

Val  Gly  Cys  Cys  Phe  Ala  Ala  Pro  Ile  Gly
                    255                       260

Gly  Val  Leu  Phe  Ser  Ile  Glu  Val  Thr  Ser
                    265                       270

Thr  Phe  Phe  Ala  Val  Arg  Asn  Tyr  Trp  Arg
                    275                       280

Gly  Phe  Phe  Ala  Ala  Thr  Phe  Ser  Ala  Phe
                    285                       290

Ile  Phe  Arg  Val  Leu  Ala  Val  Trp  Asn  Arg
```

|     |     |     |     |     |     |     |     |     |     |
|-----|-----|-----|-----|-----|-----|-----|-----|-----|-----|
|     |     |     |     | 295 |     |     |     | 300 |     |
| Asp | Glu | Glu | Thr | Ile<br>305 | Thr | Ala | Leu | Phe | Lys<br>310 |
| Thr | Arg | Phe | Arg | Leu<br>315 | Asp | Phe | Pro | Phe | Asp<br>320 |
| Leu | Gln | Glu | Leu | Pro<br>325 | Ala | Phe | Ala | Val | Ile<br>330 |
| Gly | Ile | Ala | Ser | Gly<br>335 | Phe | Gly | Gly | Ala | Leu<br>340 |
| Phe | Val | Tyr | Leu | Asn<br>345 | Arg | Lys | Ile | Val | Gln<br>350 |
| Val | Met | Arg | Lys | Gln<br>355 | Lys | Thr | Ile | Asn | Arg<br>360 |
| Phe | Leu | Met | Arg | Lys<br>365 | Arg | Leu | Leu | Phe | Pro<br>370 |
| Ala | Leu | Val | Thr | Leu<br>375 | Leu | Ile | Ser | Thr | Leu<br>380 |
| Thr | Phe | Pro | Pro | Gly<br>385 | Phe | Gly | Gln | Phe | Met<br>390 |
| Ala | Gly | Gln | Leu | Ser<br>395 | Gln | Lys | Glu | Thr | Leu<br>400 |
| Val | Thr | Leu | Phe | Asp<br>405 | Asn | Arg | Thr | Trp | Val<br>410 |
| Arg | Gln | Gly | Leu | Val<br>415 | Glu | Glu | Leu | Glu | Pro<br>420 |
| Pro | Ser | Thr | Ser | Gln<br>425 | Ala | Trp | Ser | Pro | Pro<br>430 |
| Arg | Ala | Asn | Val | Phe<br>435 | Leu | Thr | Leu | Val | Ile<br>440 |
| Phe | Ile | Leu | Met | Lys<br>445 | Phe | Trp | Met | Ser | Ala<br>450 |
| Leu | Ala | Thr | Thr | Ile<br>455 | Pro | Val | Pro | Cys | Gly<br>460 |
| Ala | Phe | Met | Pro | Val<br>465 | Phe | Val | Ile | Gly | Ala<br>470 |
| Ala | Phe | Gly | Arg | Leu<br>475 | Val | Gly | Glu | Ser | Met<br>480 |
| Ala | Ala | Trp | Phe | Pro<br>485 | Asp | Gly | Ile | His | Thr<br>490 |
| Asp | Ser | Ser | Thr | Tyr<br>495 | Arg | Ile | Val | Pro | Gly<br>500 |
| Gly | Tyr | Ala | Val | Val<br>505 | Gly | Ala | Ala | Ala | Leu<br>510 |
| Ala | Gly | Ala | Val | Thr<br>515 | His | Thr | Val | Ser | Thr<br>520 |
| Ala | Val | Ile | Val | Phe<br>525 | Glu | Leu | Thr | Gly | Gln<br>530 |
| Ile | Ala | His | Ile | Leu<br>535 | Pro | Val | Met | Ile | Ala<br>540 |
| Val | Ile | Leu | Ala | Asn<br>545 | Ala | Val | Ala | Gln | Ser<br>550 |
| Leu | Gln | Pro | Ser | Leu<br>555 | Tyr | Asp | Ser | Ile | Ile<br>560 |

-continued

| | | | | | | | | |
|---|---|---|---|---|---|---|---|---|
| Arg | Ile | Lys | Lys | Leu 565 | Pro | Tyr | Leu | Pro Glu 570 |
| Leu | Gly | Trp | Gly | Arg 575 | His | Gln | Gln | Tyr Arg 580 |
| Val | Arg | Val | Glu | Asp 585 | Ile | Met | Val | Arg Asp 590 |
| Val | Pro | His | Val | Ala 595 | Leu | Ser | Cys | Thr Phe 600 |
| Arg | Asp | Leu | Arg | Leu 605 | Ala | Leu | His | Arg Thr 610 |
| Lys | Gly | Arg | Thr | Leu 615 | Ala | Leu | Val | Glu Ser 620 |
| Pro | Glu | Ser | Met | Ile 625 | Leu | Leu | Gly | Ser Ile 630 |
| Glu | Arg | Thr | Gln | Val 635 | Val | Ala | Leu | Leu Ala 640 |
| Ala | Gln | Leu | Ser | Pro 645 | Ala | Arg | Arg | Arg Gln 650 |
| Ser | Lys | Gln | Lys | Arg 655 | Arg | Val | Ala | His Thr 660 |
| Ser | Pro | Pro | Ser | Cys 665 | Gln | Glu | Ser | Pro Pro 670 |
| Ser | Pro | Glu | Thr | Ser 675 | Val | Cys | Phe | Gln Val 680 |
| Lys | Ala | Glu | Asp | Ala 685 | Gln | Gly | Glu | Pro His 690 |
| Lys | Pro | Leu | Lys | Pro 695 | Ala | Leu | Lys | Arg Gly 700 |
| Cys | Ser | Asn | Ser | Val 705 | Asn | Leu | Gly | Glu Ser 710 |
| Pro | Thr | Gly | His | Val 715 | Glu | Ser | Ala | Gly Ile 720 |
| Ala | Leu | Arg | Ser | Leu 725 | Phe | Cys | Gly | Ser Pro 730 |
| Pro | Pro | Glu | Ala | Ala 735 | Ser | Glu | Ser | Glu Lys 740 |
| Ser | Glu | Ser | Ser | Glu 745 | Lys | Arg | Lys | Ser Lys 750 |
| Arg | Val | Arg | Ile | Ser 755 | Leu | Ala | Ser | Asp Ser 760 |
| Asp | Leu | Glu | Gly | Glu 765 | Met | Ser | Pro | Glu Glu 770 |
| Ile | Leu | Glu | Trp | Glu 775 | Glu | Gln | Gln | Leu Asp 780 |
| Glu | Pro | Val | Asn | Phe 785 | Ser | Asp | Cys | Lys Ile 790 |
| Asp | Pro | Ala | Pro | Phe 795 | Gln | Leu | Val | Glu Arg 800 |
| Thr | Ser | Leu | His | Lys 805 | Thr | His | Thr | Ile Phe 810 |
| Ser | Leu | Leu | Gly | Val 815 | Asp | His | Ala | Tyr Val 820 |
| Thr | Ser | Ile | Gly | Arg 825 | Leu | Ile | Gly | Ile Val 830 |

| | | | | | | | | | |
|---|---|---|---|---|---|---|---|---|---|
| Thr | Leu | Lys | Glu | Leu 835 | Arg | Lys | Ala | Ile | Glu 840 |
| Gly | Ser | Val | Thr | Ala 845 | Gln | Gly | Val | Lys | Val 850 |
| Arg | Pro | Pro | Leu | Ala 855 | Ser | Phe | Arg | Asp | Ser 860 |
| Ala | Thr | Ser | Ser | Ser 865 | Asp | Thr | Glu | Thr | Thr 870 |
| Glu | Val | His | Ala | Leu 875 | Trp | Gly | Pro | Arg | Ser 880 |
| Arg | His | Gly | Leu | Pro 885 | Arg | Glu | Gly | Ser | Pro 890 |
| Ser | Asp | Ser | Asp | Asp 895 | Lys | Cys | Gln | | |

(2) INFORMATION FOR SEQ ID NO:2:

(i) SEQUENCE CHARACTERISTICS:
        (A) LENGTH: 907 amino acids
        (B) TYPE: amino acid
        (D) TOPOLOGY: linear (ii) MOLECULE TYPE: protein (ix) FEATURE:
        (A) NAME/KEY: Rat Brain CIC-2

(xi) SEQUENCE DESCRIPTION: SEQ ID NO:2:

| | | | | | | | | | |
|---|---|---|---|---|---|---|---|---|---|
| Met | Ala | Ala | Ala | Thr 5 | Ala | Ala | Ala | Ala | Thr 10 |
| Val | Ala | Gly | Glu | Gly 15 | Met | Glu | Pro | Arg | Ala 20 |
| Leu | Gln | Tyr | Glu | Gln 25 | Thr | Leu | Met | Tyr | Gly 30 |
| Arg | Tyr | Thr | Gln | Glu 35 | Leu | Gly | Ala | Phe | Ala 40 |
| Lys | Glu | Glu | Ala | Ala 45 | Arg | Ile | Arg | Leu | Gly 50 |
| Gly | Pro | Glu | Pro | Trp 55 | Lys | Gly | Ser | Pro | Ser 60 |
| Ala | Arg | Ala | Thr | Pro 65 | Glu | Leu | Leu | Glu | Tyr 70 |
| Gly | Gln | Ser | Arg | Cys 75 | Ala | Arg | Cys | Arg | Ile 80 |
| Cys | Ser | Val | Arg | Cys 85 | His | Lys | Phe | Leu | Val 90 |
| Ser | Arg | Val | Gly | Glu 95 | Asp | Trp | Ile | Phe | Leu 100 |
| Val | Leu | Leu | Gly | Leu 105 | Leu | Met | Ala | Leu | Val 110 |
| Ser | Trp | Ala | Met | Asp 115 | Tyr | Ala | Ile | Ala | Val 120 |
| Cys | Leu | Gln | Ala | Gln 125 | Gln | Trp | Met | Ser | Arg 130 |
| Gly | Leu | Asn | Thr | Asn 135 | Ile | Leu | Leu | Gln | Tyr 140 |
| Leu | Ala | Trp | Val | Thr | Tyr | Pro | Val | Val | Leu |

```
                               145                           150
Ile  Thr  Phe  Ser  Ala  Gly  Phe  Thr  Gln  Ile
                    155                           160
Leu  Ala  Pro  Gln  Ala  Val  Gly  Ser  Gly  Ile
                    165                           170
Pro  Glu  Met  Lys  Thr  Ile  Leu  Arg  Gly  Val
                    175                           180
Val  Leu  Lys  Glu  Tyr  Leu  Thr  Leu  Lys  Thr
                    185                           190
Phe  Val  Ala  Lys  Val  Ile  Gly  Leu  Thr  Cys
                    195                           200
Ala  Leu  Gly  Ser  Gly  Met  Pro  Leu  Gly  Lys
                    205                           210
Glu  Gly  Pro  Phe  Val  His  Ile  Ala  Ser  Met
                    215                           220
Cys  Ala  Ala  Leu  Leu  Ser  Lys  Phe  Leu  Ser
                    225                           230
Leu  Phe  Gly  Gly  Ile  Tyr  Glu  Asn  Glu  Ser
                    235                           240
Arg  Asn  Thr  Glu  Met  Leu  Ala  Ala  Ala  Cys
                    245                           250
Ala  Val  Gly  Val  Gly  Cys  Cys  Phe  Ala  Ala
                    255                           260
Pro  Ile  Gly  Gly  Val  Leu  Phe  Ser  Ile  Glu
                    265                           270
Val  Thr  Ser  Thr  Phe  Phe  Ala  Val  Arg  Asn
                    275                           280
Tyr  Trp  Arg  Gly  Phe  Phe  Ala  Ala  Thr  Phe
                    285                           290
Ser  Ala  Phe  Ile  Phe  Arg  Val  Leu  Ala  Val
                    295                           300
Trp  Asn  Arg  Asp  Glu  Glu  Thr  Ile  Thr  Ala
                    305                           310
Leu  Phe  Lys  Thr  Arg  Phe  Arg  Leu  Asp  Phe
                    315                           320
Pro  Phe  Asp  Leu  Gln  Glu  Leu  Pro  Ala  Phe
                    325                           330
Ala  Val  Ile  Gly  Ile  Ala  Ser  Gly  Phe  Gly
                    335                           340
Gly  Ala  Leu  Phe  Val  Tyr  Leu  Asn  Arg  Lys
                    345                           350
Ile  Val  Gln  Val  Met  Arg  Lys  Gln  Lys  Thr
                    355                           360
Ile  Asn  Arg  Phe  Leu  Met  Lys  Lys  Arg  Leu
                    365                           370
Leu  Phe  Pro  Ala  Leu  Val  Thr  Leu  Leu  Ile
                    375                           380
Ser  Thr  Leu  Thr  Phe  Pro  Pro  Gly  Phe  Gly
                    385                           390
Gln  Phe  Met  Ala  Gly  Gln  Leu  Ser  Gln  Lys
                    395                           400
Glu  Thr  Leu  Val  Thr  Leu  Phe  Asp  Asn  Arg
                    405                           410
```

-continued

| | | | | | | | | |
|---|---|---|---|---|---|---|---|---|
| Thr | Trp | Val | Arg | Gln 415 | Gly | Leu | Val | Glu 420 |
| Leu | Gly | Ala | Pro | Ser 425 | Thr | Ser | Gln | Ala 430 Trp |
| Ser | Pro | Pro | Arg | Ala 435 | Asn | Val | Phe | Leu 440 Thr |
| Leu | Val | Ile | Phe | Ile 445 | Leu | Met | Lys | Phe 450 Trp |
| Met | Ser | Ala | Leu | Ala 455 | Thr | Thr | Ile | Pro 460 Val |
| Pro | Cys | Gly | Ala | Phe 465 | Met | Pro | Val | Phe 470 Val |
| Ile | Gly | Ala | Ala | Phe 475 | Gly | Arg | Leu | Val 480 Gly |
| Glu | Ser | Met | Ala | Ala 485 | Trp | Phe | Pro | Asp 490 Gly |
| Ile | His | Thr | Asp | Ser 495 | Ser | Thr | Tyr | Arg 500 Ile |
| Val | Pro | Gly | Gly | Tyr 505 | Ala | Val | Val | Gly 510 Ala |
| Ala | Ala | Leu | Ala | Gly 515 | Ala | Val | Thr | His 520 Thr |
| Val | Ser | Thr | Ala | Val 525 | Ile | Val | Phe | Glu 530 Leu |
| Thr | Gly | Gln | Ile | Ala 535 | His | Ile | Leu | Pro 540 Val |
| Met | Ile | Ala | Val | Ile 545 | Leu | Ala | Asn | Ala 550 Val |
| Ala | Gln | Ser | Leu | Gln 555 | Pro | Ser | Leu | Tyr 560 Asp |
| Ser | Ile | Ile | Arg | Ile 565 | Lys | Lys | Leu | Pro 570 Tyr |
| Leu | Pro | Glu | Leu | Gly 575 | Trp | Gly | Arg | His 580 Gln |
| Gln | Tyr | Arg | Val | Arg 585 | Val | Glu | Asp | Ile 590 Met |
| Val | Arg | Asp | Val | Pro 595 | His | Val | Ala | Leu 600 Ser |
| Cys | Thr | Phe | Arg | Asp 605 | Leu | Arg | Leu | Ala 610 Leu |
| His | Arg | Thr | Lys | Gly 615 | Arg | Met | Leu | Ala 620 Leu |
| Val | Glu | Ser | Pro | Glu 625 | Ser | Met | Ile | Leu 630 Leu |
| Gly | Ser | Ile | Glu | Arg 635 | Ser | Gln | Val | Val 640 Ala |
| Leu | Leu | Gly | Ala | Gln 645 | Leu | Ser | Pro | Ala 650 Arg |
| Arg | Arg | Gln | His | Met 655 | Gln | Lys | Leu | Arg 660 Lys |
| Ala | Gln | Met | Ser | Pro 665 | Pro | Ser | Asp | Gln 670 Glu |
| Ser | Pro | Pro | Ser | Ser 675 | Glu | Thr | Ser | Ile 680 Arg |

| | | | | | | | | | |
|---|---|---|---|---|---|---|---|---|---|
| Phe | Gln | Val | Asn | Thr 685 | Glu | Asp | Ser | Gly | Phe 690 |
| Pro | Gly | Ala | His | Gly 695 | Gln | Thr | His | Lys | Pro 700 |
| Leu | Lys | Pro | Ala | Leu 705 | Lys | Arg | Gly | Pro | Ser 710 |
| Asn | Ala | Thr | Ser | Leu 715 | Gln | Glu | Gly | Thr | Thr 720 |
| Gly | Asn | Met | Glu | Ser 725 | Ala | Gly | Ile | Ala | Leu 730 |
| Arg | Ser | Leu | Phe | Cys 735 | Gly | Ser | Pro | Pro | Leu 740 |
| Glu | Ser | Thr | Thr | Ser 745 | Glu | Leu | Glu | Lys | Ser 750 |
| Glu | Ser | Cys | Asp | Lys 755 | Arg | Lys | Leu | Lys | Arg 760 |
| Val | Arg | Ile | Ser | Leu 765 | Ala | Ser | Asp | Ser | Asp 770 |
| Leu | Glu | Gly | Lys | Met 775 | Ser | Pro | Glu | Glu | Ile 780 |
| Leu | Glu | Trp | Glu | Glu 785 | Gln | Gln | Leu | Asp | Glu 790 |
| Pro | Val | Asn | Phe | Ser 795 | Asp | Cys | Lys | Ile | Asp 800 |
| Pro | Ala | Pro | Phe | Gln 805 | Leu | Val | Glu | Arg | Thr 810 |
| Ser | Leu | His | Lys | Thr 815 | His | Thr | Ile | Phe | Ser 820 |
| Leu | Leu | Gly | Val | Asp 825 | His | Ala | Tyr | Val | Thr 830 |
| Ser | Ile | Gly | Arg | Leu 835 | Ile | Gly | Ile | Val | Thr 840 |
| Leu | Lys | Glu | Leu | Arg 845 | Lys | Ala | Ile | Glu | Gly 850 |
| Ser | Val | Thr | Ala | Gln 855 | Gly | Val | Lys | Val | Arg 860 |
| Pro | Pro | Leu | Ala | Ser 865 | Phe | Arg | Asp | Ser | Ala 870 |
| Thr | Ser | Ser | Ser | Asp 875 | Thr | Glu | Thr | Thr | Glu 880 |
| Val | His | Ala | Leu | Trp 885 | Gly | Pro | Arg | Ser | Arg 890 |
| His | Gly | Leu | Pro | Arg 895 | Glu | Gly | Thr | Pro | Ser 900 |
| Asp | Ser | Asp | Asp | Lys 905 | Cys | Gln | | | |

(2) INFORMATION FOR SEQ ID NO:3:

(i) SEQUENCE CHARACTERISTICS:
        (A) LENGTH: 3186 base pairs
        (B) TYPE: nucleic acid
        (C) STRANDEDNESS: single
        (D) TOPOLOGY: linear (ii) MOLECULE TYPE: Genomic DNA (ix) FEATURE:
    (A) NAME/KEY: Human Gastric CIC-2

(xi) SEQUENCE DESCRIPTION: SEQ ID NO:3:

| | | | |
|---|---|---|---|
| AGTCCAGGAC AGAGCCGGAA CCGCCGAGGG AGGCGAGAGG | | | 40 |
| GCAGTGCGCG GAG ATG GCG GCC GCG GCG GCG GAG GAA GGG ATG | | | 83 |
| GAG CCA CGG GCG CTG CAG CAC GAG CAG ACC CTG ATG TAT GGC | | | 125 |
| CGG TAC ACT CAG GAC CTT GGG GCC TTT GCC AAA GAG GAA GCT | | | 167 |
| GCT CGG ATT CGC CTG GGA GGG CCT GAA CCC TGG AAA GGT CCC | | | 209 |
| CCT TCC TCT CGG GCT GCC CCA GAG CTC TTG GAA TAT GGA CGG | | | 251 |
| AGC CGT TGC GCC CGA TGC CGC GTC TGT TCT GTC CGC TGC CAC | | | 293 |
| AAG TTC CTA GTA TCC AGG GTT GGT GAA GAT TGG ATC TTC CTG | | | 335 |
| GTC CTG CTG GGG CTT CTC ATG GCA TTG TCA GCT GGG TCA ATG | | | 377 |
| GAC TAT GCC ATT GCT GCC TGT CTG CAA GCC AGC AGT GGA TGG | | | 419 |
| TCC CGG GGC TTG AAC ACC AGC ATC TTG CTC CAG TAC CTG GCC | | | 461 |
| TGG GTC ACC TAC CCT GTT GTC CTC ATC ACT TTC TCA GCC GGA | | | 503 |
| TTC ACA CAG ATC CTG GCC CCT CAG GCT GTC GGC TCT GGC ATC | | | 545 |
| CCT GAG ATG AAG ACC ATC TTG CGG GGA GTG GTG CTG AAA GAA | | | 587 |
| TAC CTC ACA CTC AAG ACC TTT ATA GCT AAG GTC ATT GGG CTG | | | 629 |
| ACC TGC GCC CTA GGC AGC GGG ATG CCG CTT GGC AAA GAG GGC | | | 671 |
| CCT TTT GTG CAT ATC GCA AGC ATG TGT GCT GCC CTT CTC AGC | | | 713 |
| AAG TTC CTC TCC CTC TTT GGG GGT ATC TAT GAG AAT GAA TCC | | | 755 |
| CGG AAC ACA GAG ATG CTG GCT GCC GCC TGT GCC GTG GGG GTG | | | 797 |
| GGC TGC TGC TTC GCG GCA CCT ATT GGA GGC GTC CTC TTC AGC | | | 839 |
| ATC GAG GTC ACC TCC ACC TTC TTT GCA GTG CGG AAC TAC TGG | | | 881 |
| CGG GGC TTC TTC GCT GCC ACC TTC AGT GCC TTC ATC TTC CGG | | | 923 |
| GTC TTG GCA GTC TGG AAC CGG GAT GAA GAG ACT ATT ACA GCC | | | 965 |
| CTC TTC AAA ACC CGA TTC CGG CTC GAC TTC CCC TTT GAC CTG | | | 1007 |
| CAG GAG CTG CCA GCC TTT GCT GTC ATT GGT ATT GCT AGT GGC | | | 1049 |
| TTC GGT GGA GCC CTC TTT GTC TAC CTG AAC CGG AAG ATT GTC | | | 1091 |
| CAG GTG ATG CGG AAG CAG AAA ACC ATC AAT CGC TTC CTC ATG | | | 1133 |
| AGG AAA CGC CTG CTC TTC CCG GCT CTG GTG ACC CTG CTC ATC | | | 1175 |
| TCC ACG CTG ACC TTC CCC CCT GGC TTT GGA CAG TTC ATG GCT | | | 1217 |
| GGA CAG CTC TCA CAG AAA GAG ACG CTG GTC ACC CTG TTT GAC | | | 1259 |
| AAT CGG ACG TGG GTC CGC CAG GGC CTG GTG CAG GAG CTA GAA | | | 1301 |
| CCA CCC AGC ACC TCA CAG GCC TGG AAC CCA CCA CGT GCC AAC | | | 1343 |
| GTC TTC CTC ACC CTG GTC ATC TTC ATT CTC ATG AAG TTC TGG | | | 1385 |
| ATG TCT GCA CTG GCC ACC ACC ATC CCA GTT CCC TGT GGG GCC | | | 1427 |
| TTC ATG CCT GTC TTT GTC ATT GGA GCA GCA TTT GGG GGT CTG | | | 1469 |
| GTG GGT GAA AGC ATG GCT GCC TGG TTC CCA GAT GGA ATT CAT | | | 1511 |
| ACG GAC AGC AGC ACC TAC CGG ATT GTG CCT GGG GGC TAC GCT | | | 1553 |

-continued

```
GTG GTC GGG GCA GCT GCG CTG GCA GGA GCG GTG ACA CAC ACA         1595
GTG TCC ACG GCT GTG ATC GTG TTC GAG CTC ACA GGC CAG ATT         1637
GCC CAC ATC CTG CCT GTC ATG ATC GCC GTC ATC CTG GCC AAC         1679
GCT GTC GCC CAG AGT CTG CAG CCC TCC CTC TAT GAC AGC ATC         1721
ATC CGA ATC AAG AAA CTG CCC TAC CTG CCT GAG CTC GGC TGG         1763
GGC CGC CAC CAG CAG TAC CGG GTG CGT GTG GAG GAC ATC ATG         1805
GTG CGG GAT GTT CCC CAT GTG GCC CTC AGC TGC ACC TTC CGG         1847
GAC CTG CGT TTG GCA CTG CAC AGG ACC AAG GGC CGA ATG CTG         1889
GCC CTA GTG GAG TCC CCT GAG TCC ATG ATT CTG CTG GGC TCC         1931
ATC GAG CGT TCA CAG GTG GTG GCA TTG TTG GGG GCC CAG CTG         1973
AGC CCA GCC CGC CGG CGG CAG CAC ATG CAG GAG CGC AGA GCC         2015
ACC CAG ACC TCT CCA CTA TCT GAT CAG GAG GGT CCC CCT AGC         2057
CCT GAG GCT TCT GTC TGC TTC CAG GTG AAC ACA GAA GAC TCA         2099
GCC TTC CCA GCA GCC CGG GGG GAG ACC CAC AAG CCC CTA AAG         2141
CCT GCA CTC AAG AGG GGG CCC AGT GTC ACC AGG AAC CTC GGA         2183
GAG AGT CCC ACA GGG AGC GCA GAG TCG GCA GGC ATC GCC CTC         2225
CGG AGC CTC TTC TGT GGC AGT CCA CCC CCT GAG GCT GCT TCG         2267
GAG AAG TTG GAA TCC TGT GAG AAG CGC AAG CTG AAG CGT GTC         2309
CGA ATC TCC CTG GCA AGT GAC GCG GAC CTG GAA GGC GAG ATG         2351
AGC CCT GAA GAG ATT CTG GAG TGG GAG GAG CAG CAA CTA GAT         2393
GAA CCT GTC AAC TTC AGT GAC TGC AAA ATT GAT CCT GCT CCC         2435
TTC CAG CTG GTG GAG CGG ACC TCT TTG CAC AAG ACT CAC ACT         2477
ATC TTC TCA CTG CTG GGA GTG GAC CAT GCT TAT GTC ACC AGT         2519
ATT GGC AGA CTC ATT GGA ATC GTT ACT CTA AAG GAG CTC CGG         2561
AAG GCC ATC GAG GGC TCT GTC ACA GCA CAG GGT GTG AAA GTC         2603
CGG CCG CCC CTC GCC AGC TTC CGA GAC AGT GCC ACC AGC AGC         2645
AGT GAC ACG GAG ACC ACT GAG GTG CAT GCA CTC TGG GGG CCC         2687
CAC TCC CGT CAT GGC CTC CCC GGG GAG GGC AGC CCT TCC GAC         2729
AGC GAC GAC AAA TGC CAA TGA                                     2750
GCCCCTCGTG GGTGGCCTAG GATGGTGCTA GCCATGCCCG TCAGCCCAGA          2800
ATGTGCATCT TTCATTCCTT CTGCCTTCGG AAGGCAGGAG GCAGCTACAG          2850
CTGGAGGCTG CACCCCAGCC CCCTCCAGAC CTGGGGTGCC AGCTTCTCCC          2900
AGTTCATCCT ACCTGGAATC TGACCCACTA CCCACCTGCA ACAAGTCTTC          2950
CAGAGGCAGG AAGATAGGCC CTGCCCTGGC AGGATGGGTT GGGGTCACTT          3000
GACCCCTGCT CCCCCTTTGA GGGGGAAGGG GTGGAACTAA GATGGGTTTA          3050
TAACTGGAAC CTCCAATGAC CAGACTGTAT ATAGAGATTT ACAAAGATTT          3100
TTATATTAAT TTAATAAAAC AAATTCTTAA ATAGAACAAA ATAAACACCT          3150
AATGAGCCAC TTTATATATA AAAAAAAAAA AAAAA                          3186
```

(2) INFORMATION FOR SEQ ID NO:4:

(i) SEQUENCE CHARACTERISTICS:

-continued (A) LENGTH: 898 amino acids
(B) TYPE: amino acid
(D) TOPOLOGY: linear (ii) MOLECULE TYPE: protein (ix) FEATURE:
   (A) NAME/KEY: Human Gastric ClC-2

(xi) SEQUENCE DESCRIPTION: SEQ ID NO:4:

| Met | Ala | Ala | Pro | Ala | Ala | Ala | Val | Glu |
|-----|-----|-----|-----|-----|-----|-----|-----|-----|
|     |     |     |     | 5   |     |     |     | 10  |
| Glu | Gly | Met | Glu | Pro | Arg | Ala | Leu | Gln | Tyr |
|     |     |     |     | 15  |     |     |     |     | 20 |
| Glu | Gln | Thr | Leu | Met | Tyr | Gly | Arg | Tyr | Thr |
|     |     |     |     | 25  |     |     |     |     | 30 |
| Gln | Asp | Leu | Gly | Ala | Phe | Ala | Lys | Glu | Glu |
|     |     |     |     | 35  |     |     |     |     | 40 |
| Ala | Ala | Arg | Ile | Arg | Leu | Gly | Gly | Pro | Glu |
|     |     |     |     | 45  |     |     |     |     | 50 |
| Pro | Trp | Arg | Ser | Pro | Pro | Ser | Pro | Arg | Thr |
|     |     |     |     | 55  |     |     |     |     | 60 |
| Pro | Pro | Glu | Leu | Leu | Glu | Tyr | Gly | Gln | Ser |
|     |     |     |     | 65  |     |     |     |     | 70 |
| Arg | Cys | Ala | Arg | Cys | Arg | Met | Cys | Ser | Val |
|     |     |     |     | 75  |     |     |     |     | 80 |
| Arg | Cys | His | Lys | Phe | Leu | Val | Ser | Arg | Val |
|     |     |     |     | 85  |     |     |     |     | 90 |
| Gly | Glu | Asp | Trp | Ile | Phe | Leu | Val | Leu | Leu |
|     |     |     |     | 95  |     |     |     |     | 100 |
| Gly | Leu | Leu | Met | Ala | Leu | Val | Ser | Trp | Ala |
|     |     |     |     | 105 |     |     |     |     | 110 |
| Met | Asp | Tyr | Ala | Ile | Ala | Ala | Cys | Leu | Gln |
|     |     |     |     | 115 |     |     |     |     | 120 |
| Ala | Gln | Gln | Trp | Met | Ser | Arg | Gly | Leu | Asn |
|     |     |     |     | 125 |     |     |     |     | 130 |
| Thr | Asn | Leu | Leu | Leu | Gln | Tyr | Leu | Ala | Trp |
|     |     |     |     | 135 |     |     |     |     | 140 |
| Val | Thr | Tyr | Pro | Val | Val | Leu | Ile | Thr | Phe |
|     |     |     |     | 145 |     |     |     |     | 150 |
| Ser | Ala | Gly | Phe | Thr | Gln | Ile | Leu | Ala | Pro |
|     |     |     |     | 155 |     |     |     |     | 160 |
| Gln | Ala | Val | Gly | Ser | Gly | Ile | Pro | Glu | Met |
|     |     |     |     | 165 |     |     |     |     | 170 |
| Lys | Thr | Ile | Leu | Arg | Gly | Val | Val | Leu | Lys |
|     |     |     |     | 175 |     |     |     |     | 180 |
| Glu | Tyr | Leu | Thr | Leu | Lys | Thr | Phe | Val | Ala |
|     |     |     |     | 185 |     |     |     |     | 190 |
| Lys | Val | Ile | Gly | Leu | Thr | Cys | Ala | Leu | Gly |
|     |     |     |     | 195 |     |     |     |     | 200 |
| Ser | Gly | Met | Pro | Leu | Gly | Lys | Glu | Gly | Pro |
|     |     |     |     | 205 |     |     |     |     | 210 |
| Phe | Val | His | Ile | Ala | Ser | Met | Cys | Ala | Ala |
|     |     |     |     | 215 |     |     |     |     | 220 |
| Leu | Leu | Ser | Lys | Phe | Leu | Ser | Leu | Phe | Gly |
|     |     |     |     | 225 |     |     |     |     | 230 |

| | | | | | | | | |
|---|---|---|---|---|---|---|---|---|
| Gly | Ile | Tyr | Glu | Asn<br>235 | Glu | Ser | Arg | Asn<br>240 |
| Glu | Met | Leu | Ala | Ala<br>245 | Ala | Cys | Ala | Val | Gly<br>250 |
| Val | Gly | Cys | Cys | Phe<br>255 | Ala | Ala | Pro | Ile | Gly<br>260 |
| Gly | Val | Leu | Phe | Ser<br>265 | Ile | Glu | Val | Thr | Ser<br>270 |
| Thr | Phe | Phe | Ala | Val<br>275 | Arg | Asn | Tyr | Trp | Arg<br>280 |
| Gly | Phe | Phe | Ala | Ala<br>285 | Thr | Phe | Ser | Ala | Phe<br>290 |
| Ile | Phe | Arg | Val | Leu<br>295 | Ala | Val | Trp | Asn | Arg<br>300 |
| Asp | Glu | Glu | Thr | Ile<br>305 | Thr | Ala | Leu | Phe | Lys<br>310 |
| Thr | Arg | Phe | Arg | Leu<br>315 | Asp | Phe | Pro | Phe | Asp<br>320 |
| Leu | Gln | Glu | Leu | Pro<br>325 | Ala | Phe | Ala | Val | Ile<br>330 |
| Gly | Ile | Ala | Ser | Gly<br>335 | Phe | Gly | Gly | Ala | Leu<br>340 |
| Phe | Val | Tyr | Leu | Asn<br>345 | Arg | Lys | Ile | Val | Gln<br>350 |
| Val | Met | Arg | Lys | Gln<br>355 | Lys | Thr | Ile | Asn | Arg<br>360 |
| Phe | Leu | Met | Arg | Lys<br>365 | Arg | Leu | Leu | Phe | Pro<br>370 |
| Ala | Leu | Val | Thr | Leu<br>375 | Leu | Ile | Ser | Thr | Leu<br>380 |
| Thr | Phe | Pro | Pro | Gly<br>385 | Phe | Gly | Gln | Phe | Met<br>390 |
| Ala | Gly | Gln | Leu | Ser<br>395 | Gln | Lys | Glu | Thr | Leu<br>400 |
| Val | Thr | Leu | Phe | Asp<br>405 | Asn | Arg | Thr | Trp | Val<br>410 |
| Arg | Gln | Gly | Leu | Val<br>415 | Glu | Glu | Leu | Glu | Pro<br>420 |
| Pro | Ser | Thr | Ser | Gln<br>425 | Ala | Trp | Ser | Pro | Pro<br>430 |
| Arg | Ala | Asn | Val | Phe<br>435 | Leu | Thr | Leu | Val | Ile<br>440 |
| Phe | Ile | Leu | Met | Lys<br>445 | Phe | Trp | Met | Ser | Ala<br>450 |
| Leu | Ala | Thr | Thr | Ile<br>455 | Pro | Val | Pro | Cys | Gly<br>460 |
| Ala | Phe | Met | Pro | Val<br>465 | Phe | Val | Ile | Gly | Ala<br>470 |
| Ala | Phe | Gly | Arg | Leu<br>475 | Val | Gly | Glu | Ser | Met<br>480 |
| Ala | Ala | Trp | Phe | Pro<br>485 | Asp | Gly | Ile | His | Thr<br>490 |
| Asp | Ser | Ser | Thr | Tyr<br>495 | Arg | Ile | Val | Pro | Gly<br>500 |

|     |     |     |     |     |     |     |     |     |     |
| --- | --- | --- | --- | --- | --- | --- | --- | --- | --- |
| Gly | Tyr | Ala | Val | Val<br>505 | Gly | Ala | Ala | Ala | Leu<br>510 |
| Ala | Gly | Ala | Val | Thr<br>515 | His | Thr | Val | Ser | Thr<br>520 |
| Ala | Val | Ile | Val | Phe<br>525 | Glu | Leu | Thr | Gly | Gln<br>530 |
| Ile | Ala | His | Ile | Leu<br>535 | Pro | Val | Met | Ile | Ala<br>540 |
| Val | Ile | Leu | Ala | Asn<br>545 | Ala | Val | Ala | Gln | Ser<br>550 |
| Leu | Gln | Pro | Ser | Leu<br>555 | Tyr | Asp | Ser | Ile | Ile<br>560 |
| Arg | Ile | Lys | Lys | Leu<br>565 | Pro | Tyr | Leu | Pro | Glu<br>570 |
| Leu | Gly | Trp | Gly | Arg<br>575 | His | Gln | Gln | Tyr | Arg<br>580 |
| Val | Arg | Val | Glu | Asp<br>585 | Ile | Met | Val | Arg | Asp<br>590 |
| Val | Pro | His | Val | Ala<br>595 | Leu | Ser | Cys | Thr | Phe<br>600 |
| Arg | Asp | Leu | Arg | Leu<br>605 | Ala | Leu | His | Arg | Thr<br>610 |
| Lys | Gly | Arg | Thr | Leu<br>615 | Ala | Leu | Val | Glu | Ser<br>620 |
| Pro | Glu | Ser | Met | Ile<br>625 | Leu | Leu | Gly | Ser | Ile<br>630 |
| Glu | Arg | Thr | Gln | Val<br>635 | Val | Ala | Leu | Leu | Ala<br>640 |
| Ala | Gln | Leu | Ser | Pro<br>645 | Ala | Arg | Arg | Arg | Gln<br>650 |
| Ser | Lys | Gln | Lys | Arg<br>655 | Arg | Val | Ala | His | Thr<br>660 |
| Ser | Pro | Pro | Ser | Cys<br>665 | Gln | Glu | Ser | Pro | Pro<br>670 |
| Ser | Pro | Glu | Thr | Ser<br>675 | Val | Cys | Phe | Gln | Val<br>680 |
| Lys | Ala | Glu | Asp | Ala<br>685 | Gln | Gly | Glu | Pro | His<br>690 |
| Lys | Pro | Leu | Lys | Pro<br>695 | Ala | Leu | Lys | Arg | Gly<br>700 |
| Cys | Ser | Asn | Ser | Val<br>705 | Asn | Leu | Gly | Glu | Ser<br>710 |
| Pro | Thr | Gly | His | Val<br>715 | Glu | Ser | Ala | Gly | Ile<br>720 |
| Ala | Leu | Arg | Ser | Leu<br>725 | Phe | Cys | Gly | Ser | Pro<br>730 |
| Pro | Pro | Glu | Ala | Ala<br>735 | Ser | Glu | Ser | Glu | Lys<br>740 |
| Ser | Glu | Ser | Ser | Glu<br>745 | Lys | Arg | Lys | Ser | Lys<br>750 |
| Arg | Val | Arg | Ile | Ser<br>755 | Leu | Ala | Ser | Asp | Ser<br>760 |
| Asp | Leu | Glu | Gly | Glu | Met | Ser | Pro | Glu | Glu |

-continued

| | | | | 765 | | | | | 770 |
|---|---|---|---|---|---|---|---|---|---|
| Ile | Leu | Glu | Trp | Glu | Glu | Gln | Gln | Leu | Asp |
| | | | | 775 | | | | | 780 |
| Glu | Pro | Val | Asn | Phe | Ser | Asp | Cys | Lys | Ile |
| | | | | 785 | | | | | 790 |
| Asp | Pro | Ala | Pro | Phe | Gln | Leu | Val | Glu | Arg |
| | | | | 795 | | | | | 800 |
| Thr | Ser | Leu | His | Lys | Thr | His | Thr | Ile | Phe |
| | | | | 805 | | | | | 810 |
| Ser | Leu | Leu | Gly | Val | Asp | His | Ala | Tyr | Val |
| | | | | 815 | | | | | 820 |
| Thr | Ser | Ile | Gly | Arg | Leu | Ile | Gly | Ile | Val |
| | | | | 825 | | | | | 830 |
| Thr | Leu | Lys | Glu | Leu | Arg | Lys | Ala | Ile | Glu |
| | | | | 835 | | | | | 840 |
| Gly | Ser | Val | Thr | Ala | Gln | Gly | Val | Lys | Val |
| | | | | 845 | | | | | 850 |
| Arg | Pro | Pro | Leu | Ala | Ser | Phe | Arg | Asp | Ser |
| | | | | 855 | | | | | 860 |
| Ala | Thr | Ser | Ser | Ser | Asp | Thr | Glu | Thr | Thr |
| | | | | 865 | | | | | 870 |
| Glu | Val | His | Ala | Leu | Trp | Gly | Pro | Arg | Ser |
| | | | | 875 | | | | | 880 |
| Arg | His | Gly | Leu | Pro | Arg | Glu | Gly | Ser | Pro |
| | | | | 885 | | | | | 890 |
| Ser | Asp | Ser | Asp | Asp | Lys | Cys | Gln | | |
| | | | | 895 | | | | | |